US012697116B2

(12) United States Patent　　　　　(10) Patent No.: US 12,697,116 B2
Koduri　　　　　　　　　　　　　　　(45) Date of Patent: Aug. 4, 2026

(54) SUTURE RETRIEVAL SYSTEMS AND METHODS

(71) Applicant: Anuradha Koduri, Chicago, IL (US)

(72) Inventor: Anuradha Koduri, Chicago, IL (US)

( * ) Notice: Subject to any disclaimer, the term of this patent is extended or adjusted under 35 U.S.C. 154(b) by 82 days.

(21) Appl. No.: 18/611,401

(22) Filed: Mar. 20, 2024

(65) Prior Publication Data

US 2024/0358365 A1　　　Oct. 31, 2024

Related U.S. Application Data

(60) Provisional application No. 63/453,390, filed on Mar. 20, 2023.

(51) Int. Cl.
　　*A61B 17/04*　　　　(2006.01)
(52) U.S. Cl.
　　CPC ................................ *A61B 17/0485* (2013.01)
(58) Field of Classification Search
　　CPC ............ A61B 17/0485; A61B 17/0469; A61B
　　　　　　　17/0482; A61B 17/0483; A61B 17/0625;
　　　　　　　　　　A61B 17/06; A61B 17/06066
　　See application file for complete search history.

(56) References Cited

U.S. PATENT DOCUMENTS

| | | | |
|---|---|---|---|
| 5,730,747 A | * | 3/1998 | Ek ...................... A61B 17/0469 |
| | | | 606/139 |
| 5,935,126 A | | 8/1999 | Riza |
| 7,922,744 B2 | | 4/2011 | Morris et al. |
| 8,663,250 B2 | | 3/2014 | Weber |
| 2018/0325511 A1 | | 11/2018 | Topper et al. |
| 2024/0260958 A1* | | 8/2024 | Woodward ....... A61B 17/06061 |

FOREIGN PATENT DOCUMENTS

| | | |
|---|---|---|
| CN | 203315052 U | 12/2013 |
| WO | 2022245822 A1 | 11/2022 |

OTHER PUBLICATIONS

Invitation to Pay Additional Fees from PCT App. No. PCT/US2024/020758 dated Jun. 17, 2024, 3 pages.
International Search Report and Written Opinion for PCT Application No. PCT/US2024/020758 dated Aug. 20, 2024, 15 pages.

* cited by examiner

*Primary Examiner* — Phong Son H Dang
(74) *Attorney, Agent, or Firm* — Acuity IP, LLC; Nathan S. Cassell

(57)　　　　　　ABSTRACT
A device for threading and automatically retrieving a suture is provided. The device includes a bottom handle having a channel for receiving and retaining a suture, and a top handle having a needle with an opening, the opening configured to receive and retrieve the suture as the device is moved from a closed position to an open position. Related methods of use are also provided.

3 Claims, 48 Drawing Sheets

100

202

100

204

208

206

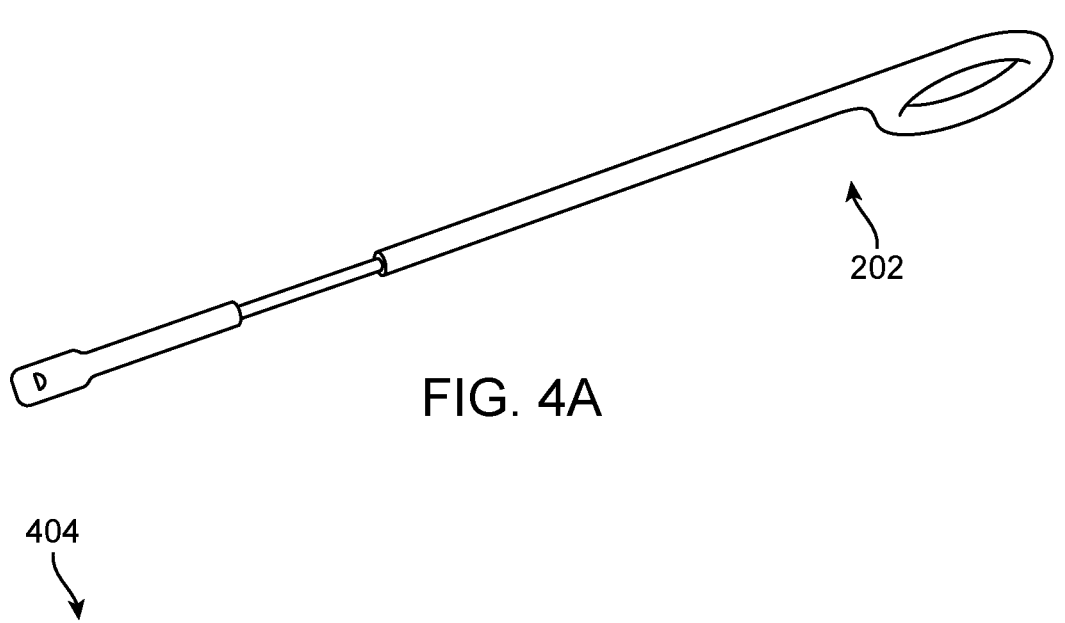
FIG. 4A
FIG. 4B
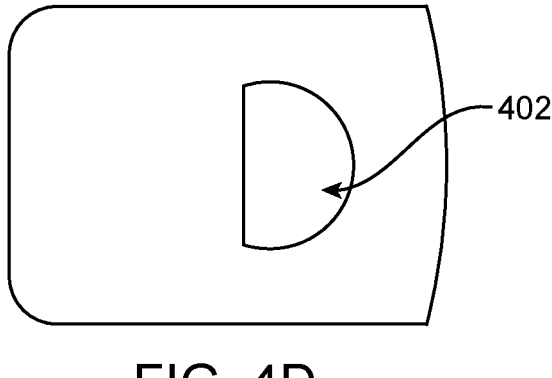
FIG. 4C
FIG. 4D

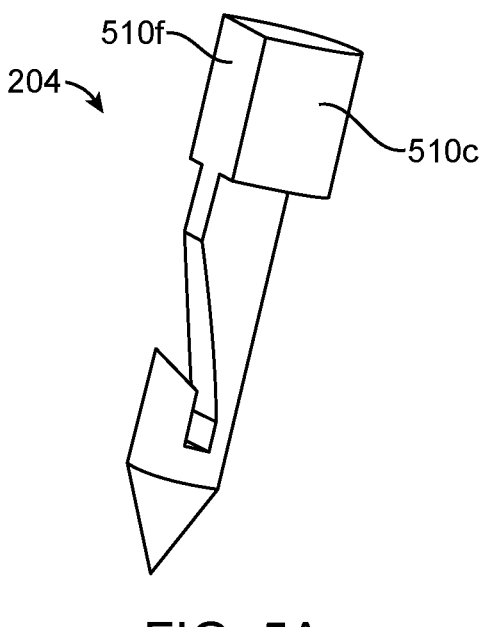
FIG. 5A
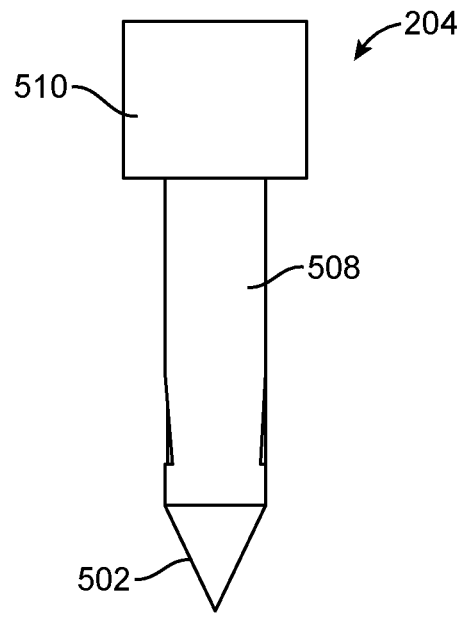
FIG. 5B
FIG. 5C
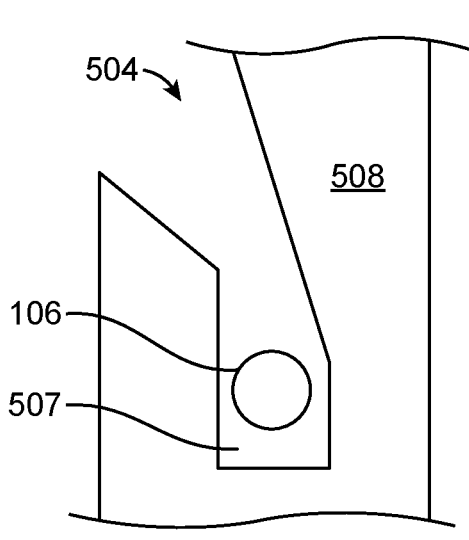
FIG. 5D

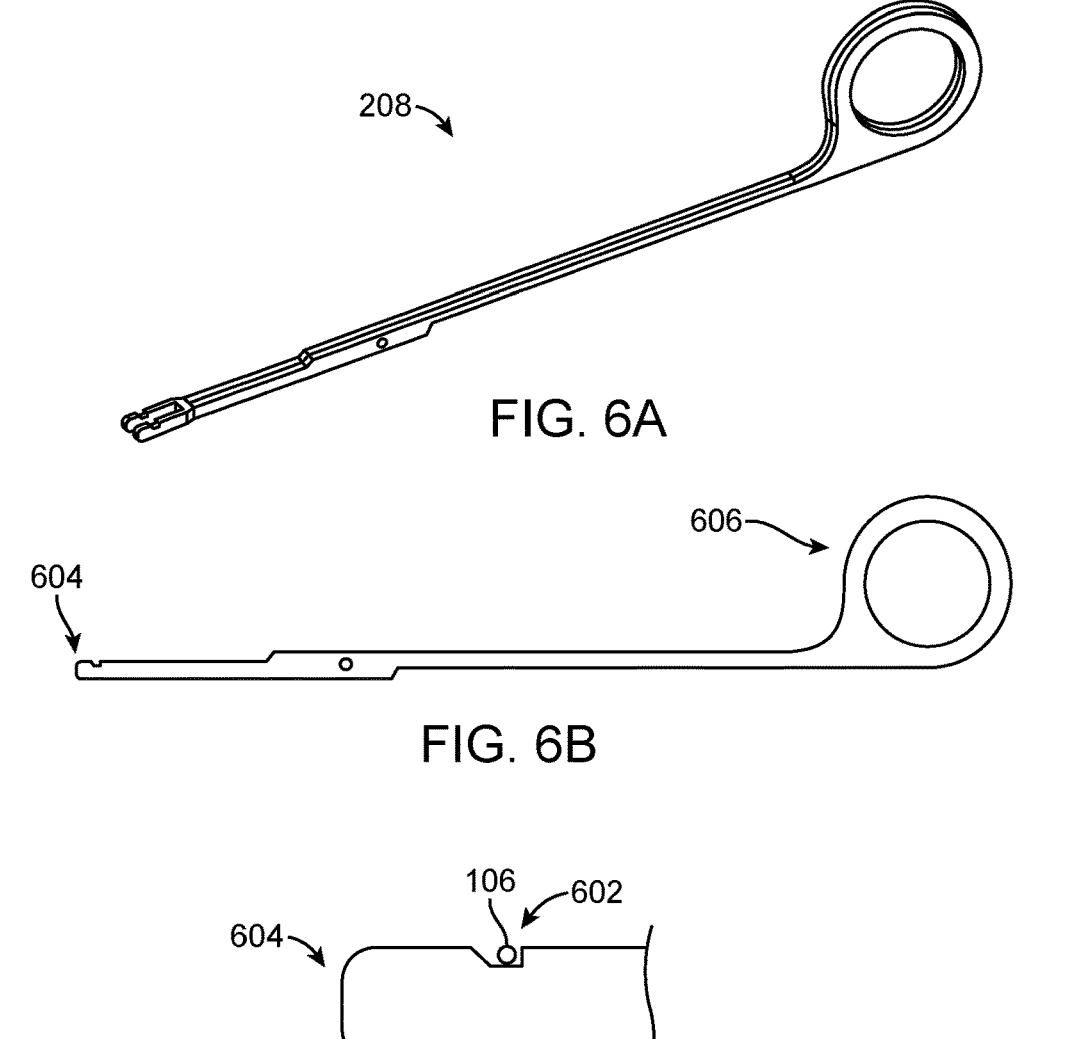
FIG. 6A
FIG. 6B
FIG. 6C
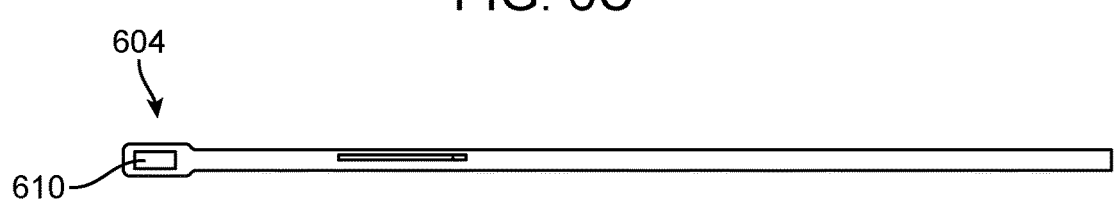
FIG. 6D
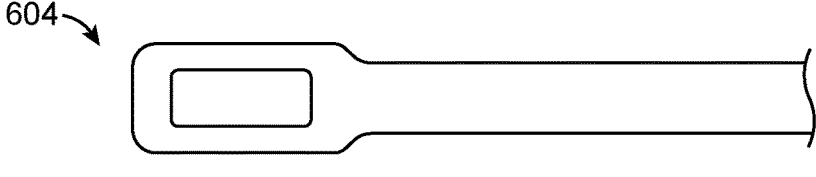
FIG. 6E

2032

2090

2080

3000

3020

3005

3030

3050

3010

4030

4005

4000

4000

4020

4005

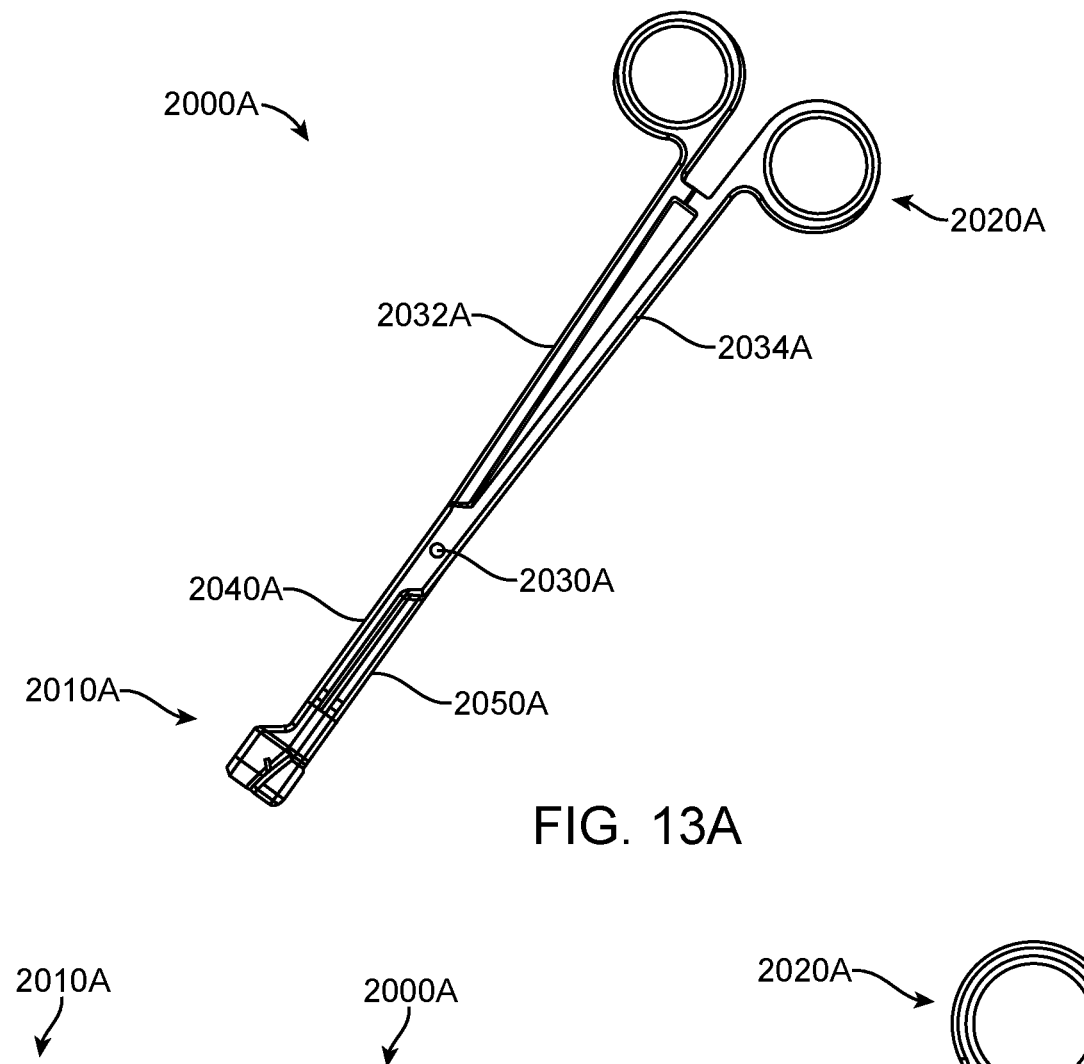
FIG. 13A
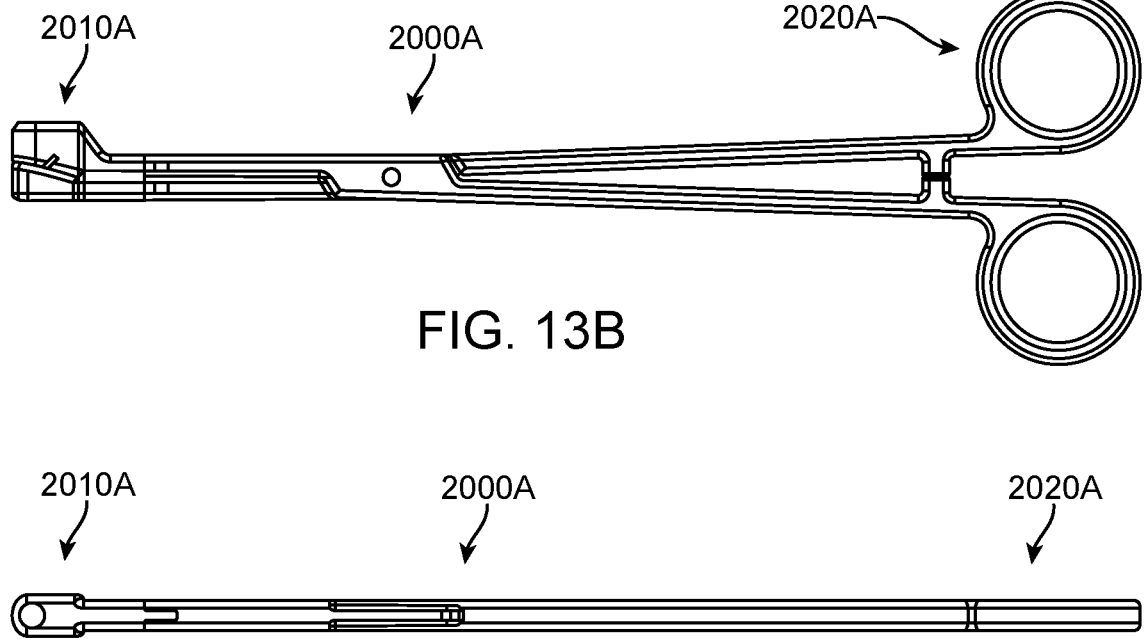
FIG. 13B
FIG. 13C

SUTURE RETRIEVAL SYSTEMS AND METHODS

CROSS-REFERENCES TO RELATED APPLICATIONS

This application claims the benefit of U.S. Provisional Patent Application No. 63/453,390 filed Mar. 20, 2023, the disclosure of which is incorporated herein by reference.

BACKGROUND OF THE INVENTION

Embodiments of the present invention related generally to the field of surgery, and in particular, to systems and methods for automatically retrieving sutures.

Sutures are used to hold body tissues together after an injury or surgery. Sutures may be used to hold together edges of a wound or surgical incision. Sutures may also be used to anchor one body tissue to another. Sutures may be used, for example, in a surgical procedure for correcting prolapse. Prolapse is a condition where the reproductive organs of a woman, such as the uterus or vagina lose their tissue support due to aging and childbirth. These reproductive organs may begin to appear outside the vaginal opening, causing a great deal of distress and discomfort to the woman. The prevalence of this condition is about 11-15% worldwide.

Sutures may be used to anchor these organs to another body tissue to correct prolapse. One such common surgery is a Sacrospinous Ligament Fixation. This involves dissecting deep in the pelvis to find the sacrospinous ligament that runs between the sacrum and the ischial spine. A suture is placed through the sacrospinous ligament and the vaginal wall that needs to be anchored, and then a knot is tied. Since surgeons work through the vaginal opening, it is a difficult procedure. In particular, putting a suture in the ligament is difficult due to the limited visibility and space.

Conventional reusable devices for administering suturing do not include automatic suture retrieval mechanisms. Instead, surgeons manually perform the suturing, which is difficult and dangerous because of the limitations posed by visibility and space. Those devices capable of retrieval of sutures are not capable of being sanitized and re-used, adding significant cost and supply-chain reliance. Thus, there is a need for improved suturing systems, methods, and devices. Embodiments of the instant invention address at least some of these outstanding needs.

BRIEF SUMMARY OF THE INVENTION

In an aspect, a device for threading and automatically retrieving a suture is provided, the device comprising a bottom handle having a channel for receiving and retaining a suture; and a top handle having a needle with an opening, the opening configured to receive and retrieve the suture as the device is moved from a closed position to an open position.

In embodiments, the bottom handle and the top handle are pivotably connected by a connector and the bottom handle and the top handle are moved toward each other to move the device to the closed position, and the bottom handle and the top handle are moved away from each other to move the device to the open position. In embodiments, the bottom handle further comprises an aperture for receiving the needle when the device is in the closed position, the channel holding the suture across the aperture. In embodiments, the channel is configured to receive any suture. In some cases, the channel can be configured to receive suture tape.

In an aspect, a system for threading and automatically retrieving a suture is provided, the system comprising a device comprising a bottom handle having a channel for receiving and retaining a suture, and a top handle having a needle with an opening, the opening configured to receive and retrieve the suture as the device is moved from a closed position to an open position.

In embodiments, the device is configured to be sterilized for re-use. In some embodiments, one or more components of a device can include a material such as stainless steel, plastic, glass filled plastic, composites, and the like.

In an aspect, a method for threading and automatically retrieving a suture using a device having a bottom handle with a channel, and a top handle with a needle having an opening is provided, the method comprising disposing the suture across a channel of the bottom handle; clasping a distal end of the device onto a tissue by moving the device from an open position to a closed position, the clasping causing the needle to pierce the tissue; and unclasping the distal end of the device from the tissue by moving the device from the closed position to the open position, the unclasping causing the opening of the needle to receive and retrieve the suture through the tissue.

In embodiments, the suture is used with the device. In embodiments, the method further comprises sterilizing the device for re-use.

In an aspect, an automatic suture device is provided comprising a distal end comprising an aperture capable of receiving a needle; a proximal end comprising a top handle and a bottom handle; and a connector comprising a hinge that is a length between the distal end and the proximal end, wherein the hinge allows for pivoting movement of the top handle and the bottom handle.

In embodiments, the automatic suture device further comprises a needle capable of being inserted into the aperture. In embodiments, the needle comprises an opening configured to receive a suture. In embodiments, the opening comprises an inclined edge configured to guide the suture through the opening.

In an aspect, a needle is provided comprising an attachment portion configured to be received by an aperture of a handle of a suture device; a tip portion configured to pierce a tissue of a patient; a body portion configured to pass through the tissue that has been pierced by the tip portion, wherein the body portion comprises an opening comprising an inclined edge that guides a suture through the opening.

In embodiments, the inclined edge comprises at least one side that comprises a sharp edge. In embodiments, the inclined edge comprises two sides that comprise a sharp edge. In embodiments, the tip comprises a sharp edge.

In embodiments, an automatic suture device can be disassembled to facilitate cleaning and sterilization.

BRIEF DESCRIPTION OF THE DRAWINGS

FIGS. 4A to 4D depict aspects of a suture device, according to embodiments of the present invention.

FIGS. 5A to 5D depict aspects of a needle of a suture device, according to embodiments of the present invention.

FIGS. 6A to 6E depict aspects of a suture device, according to embodiments of the present invention.

3

Figure 7:
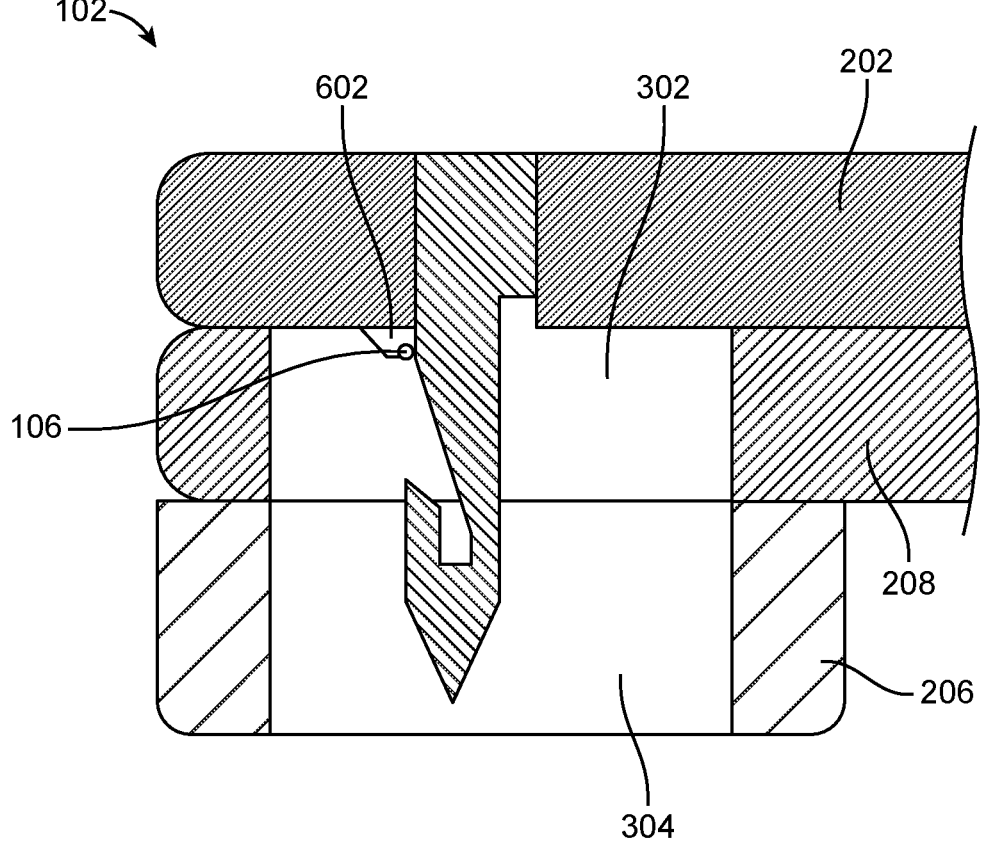

FIG. 7 illustrates aspects of a distal portion of a suture device, according to embodiments of the present invention.

FIGS. 8A to 8G depict aspects of a suture device and related methods of use, according to embodiments of the present invention.

Figure 9A:
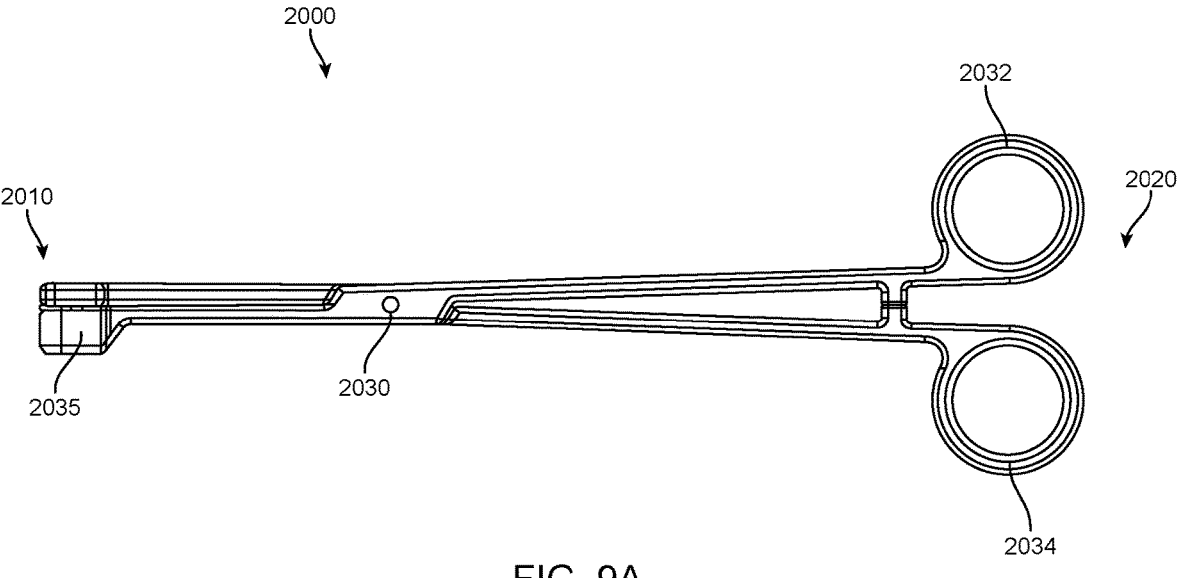
Figure 9B:
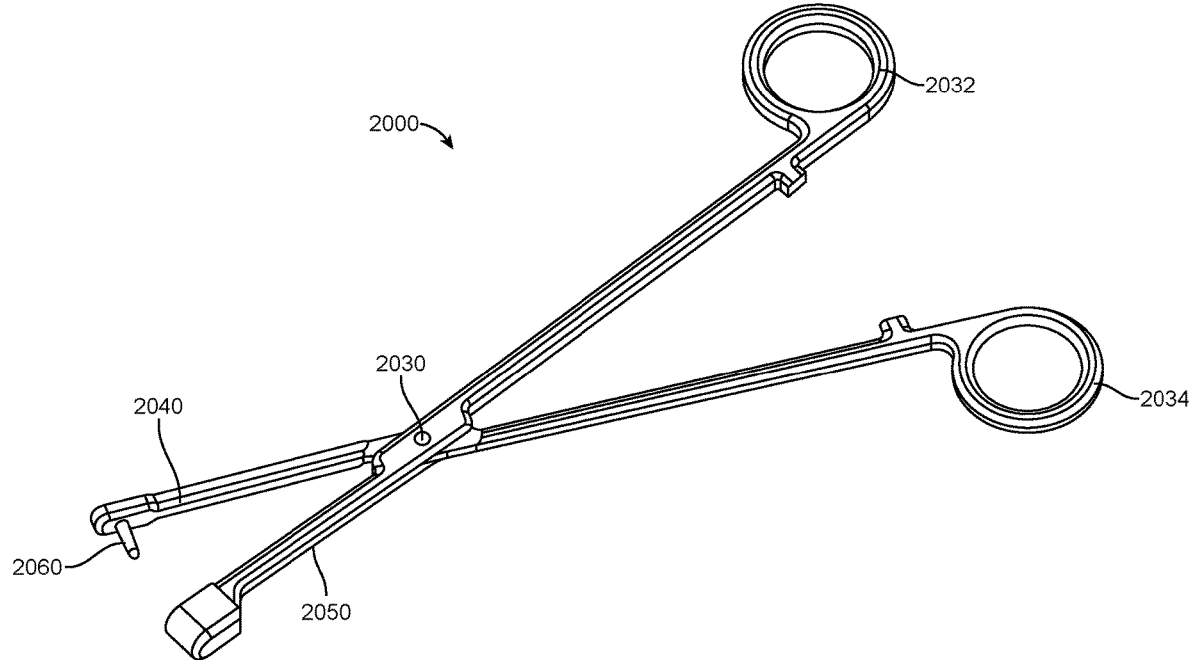
Figure 9C:
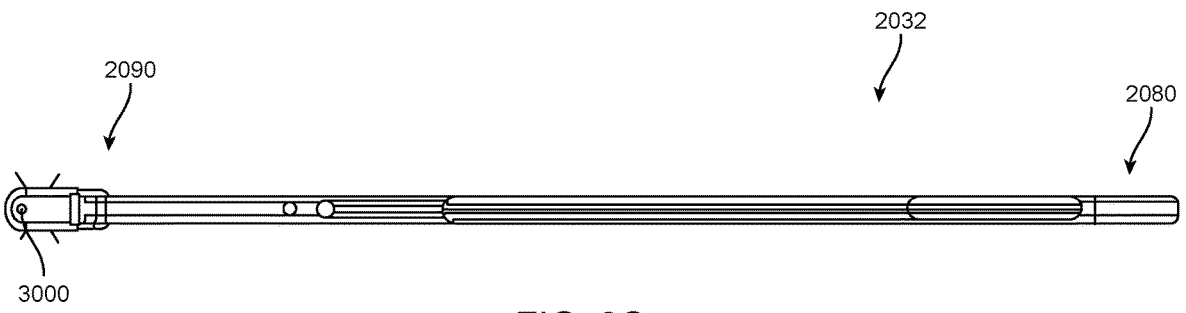

FIGS. 9A to 9C depict aspects of a suture device, according to embodiments of the present invention.

Figure 10:
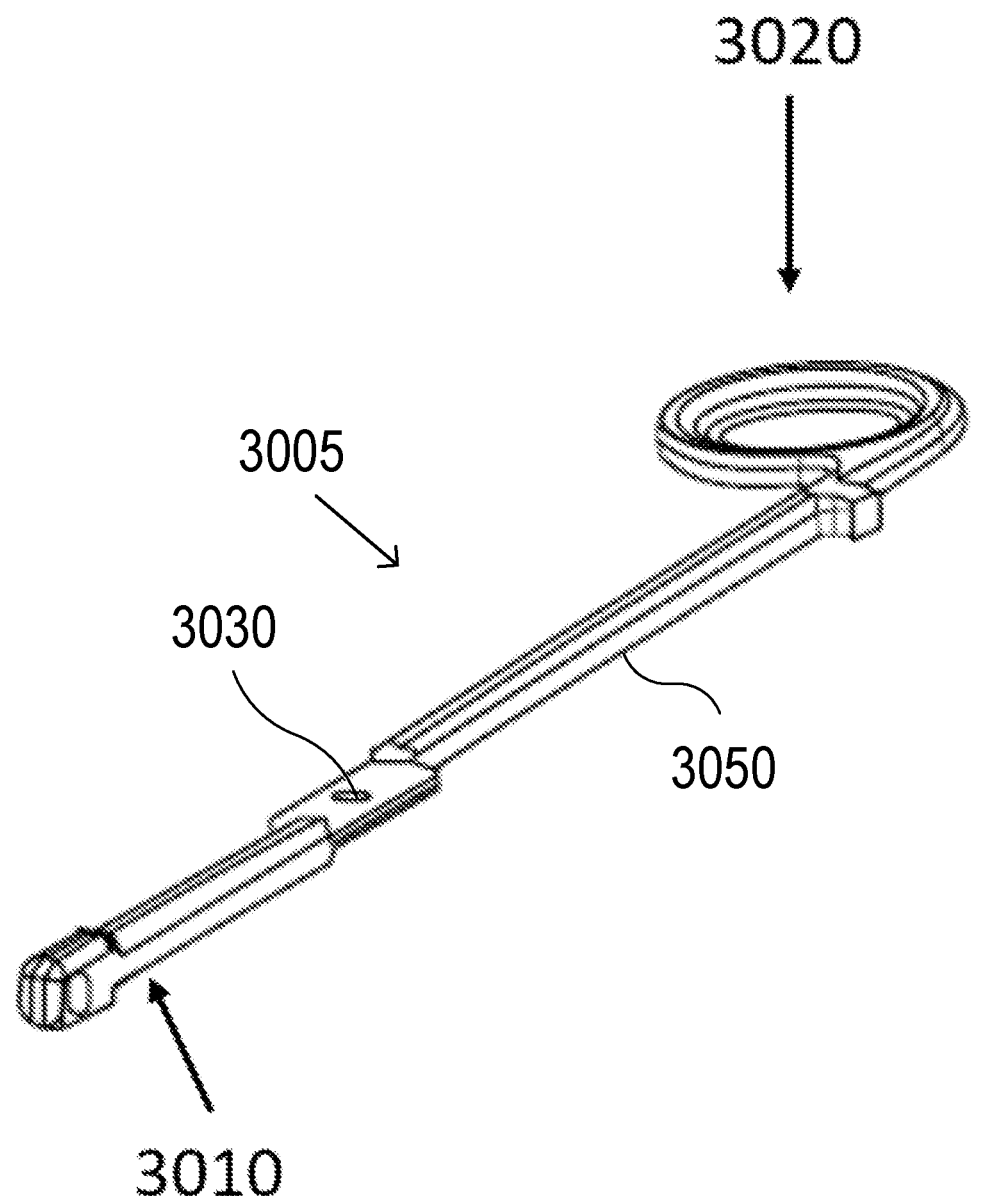

FIG. 10 illustrates aspects of a handle of a suture device, according to embodiments of the present invention.

Figure 11A:
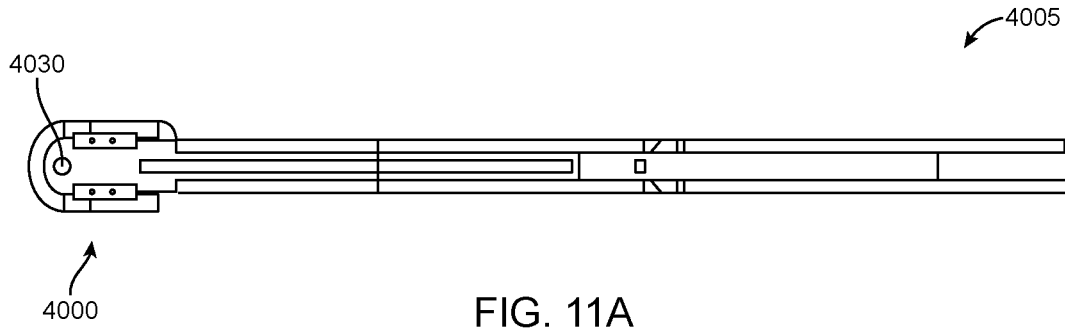
Figure 11B:
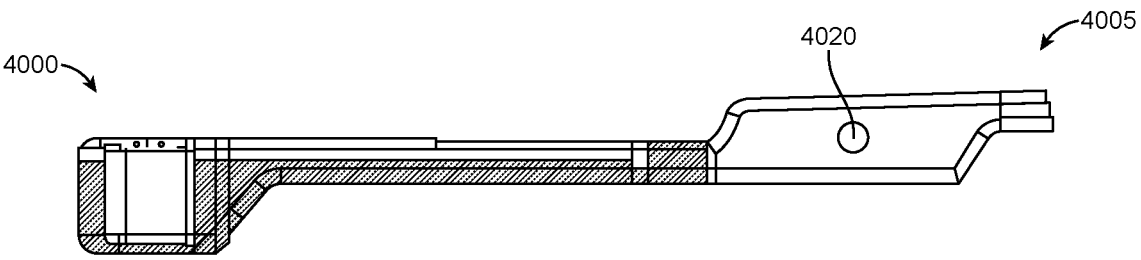

FIGS. 11A and 11B depict aspects of a handle of a suture device, according to embodiments of the present invention.

Figure 12A:
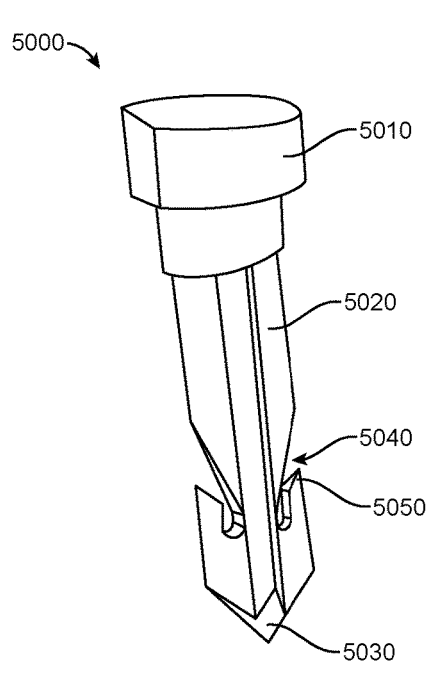
Figure 12B:
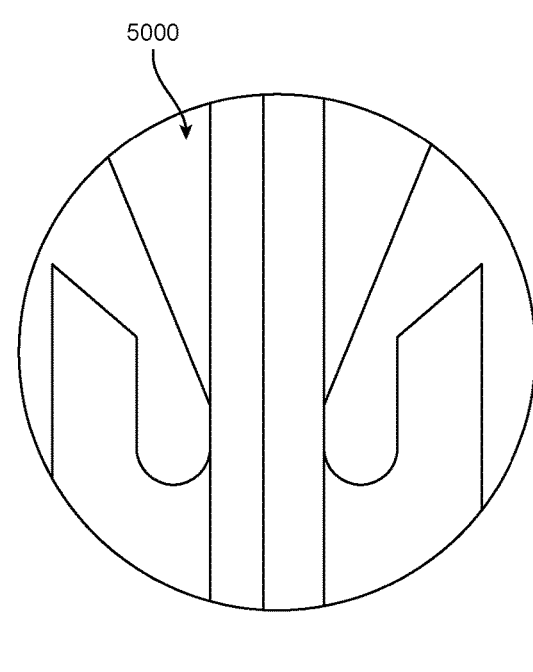

FIGS. 12A and 12B depict aspects of a needle of a suture device, according to embodiments of the present invention.

FIGS. 13A to 13L depict aspects of a suture device, according to embodiments of the present invention.

FIGS. 14A to 14I depict aspects of a suture device, according to embodiments of the present invention.

FIGS. 15A to 15D depict aspects of a needle of a suture device, according to embodiments of the present invention.

Figure 16A:
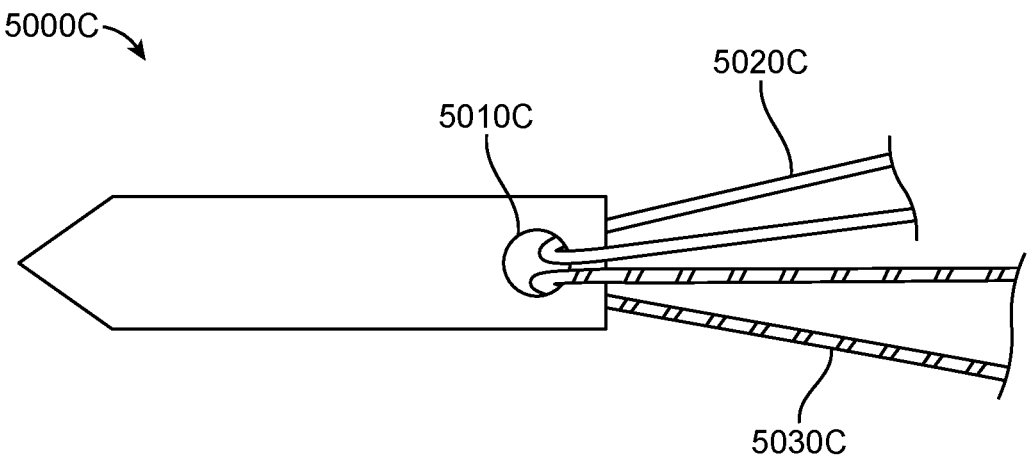
Figure 16B:
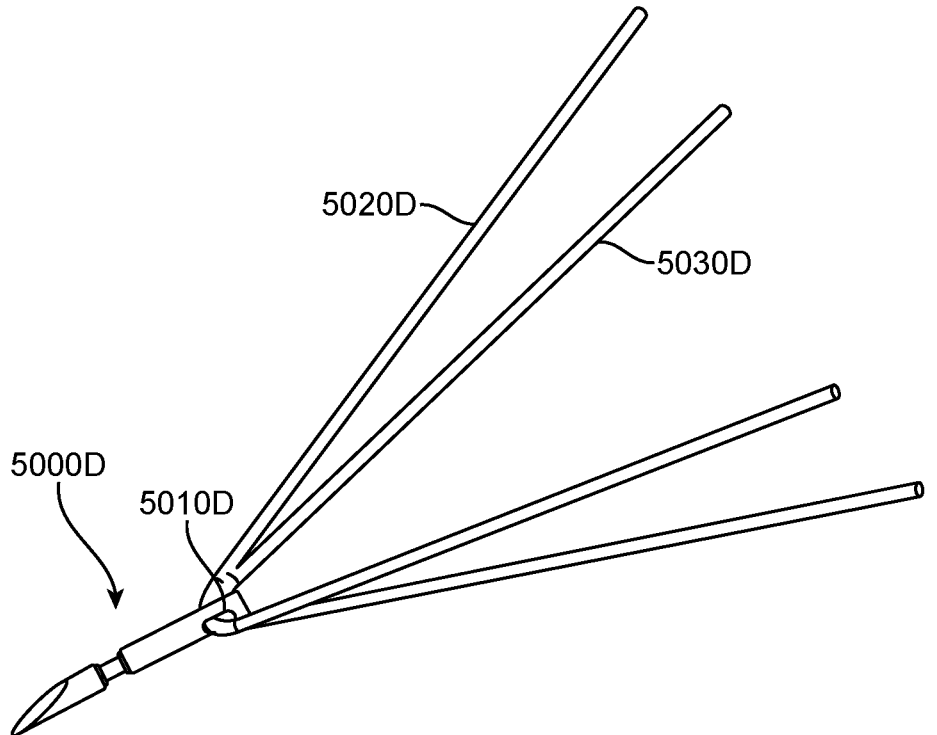

FIGS. 16A and 16B depict aspects of suture device needles, according to embodiments of the present invention.

Figure 17A:
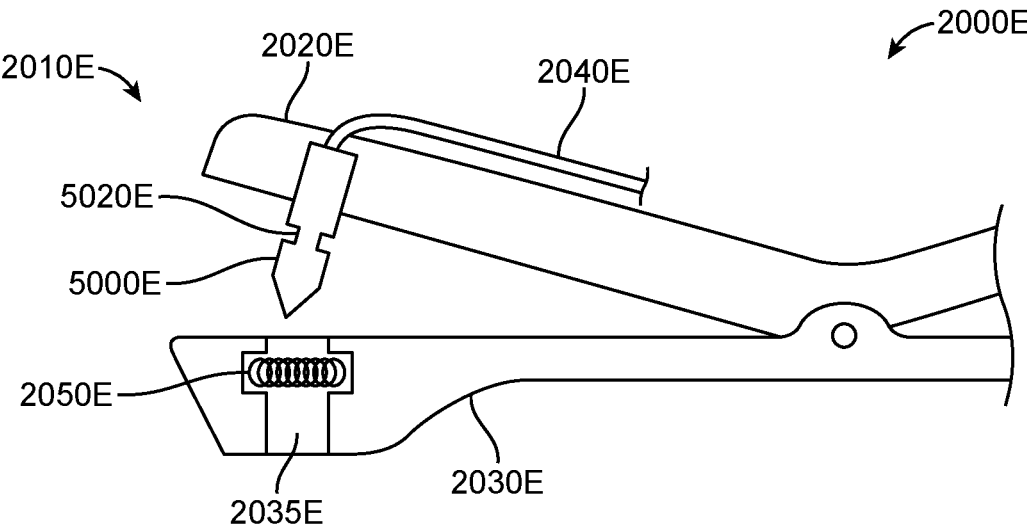
Figure 17B:
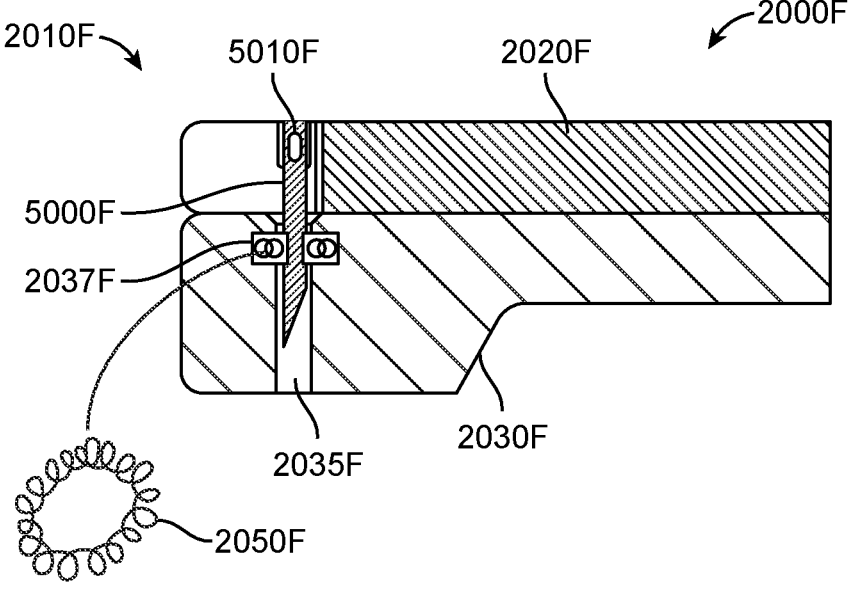

FIGS. 17A and 17B illustrate aspects of a distal portion of a suture device, according to embodiments of the present invention.

Figure 18A:
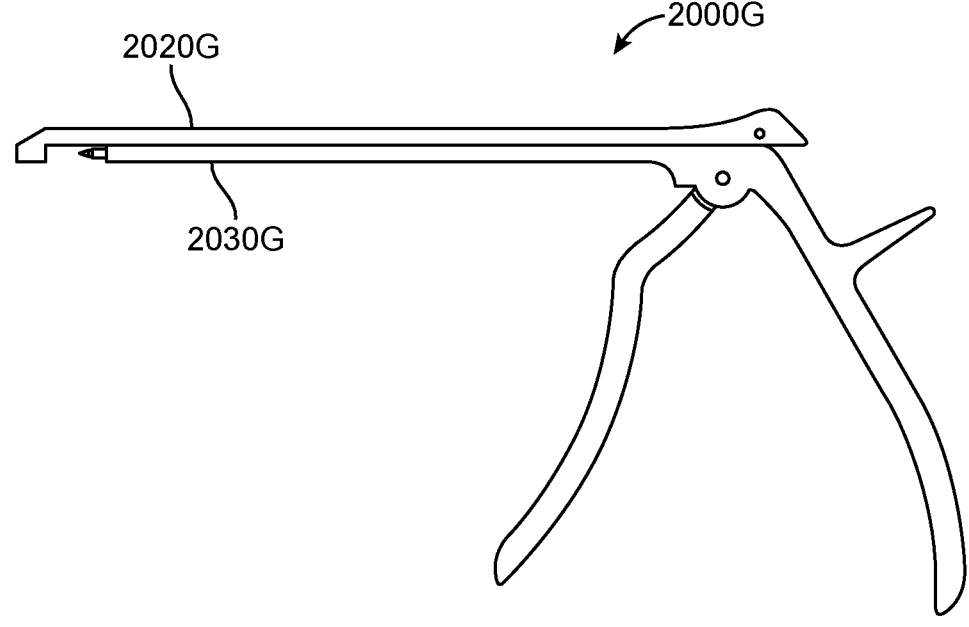
Figure 18B:
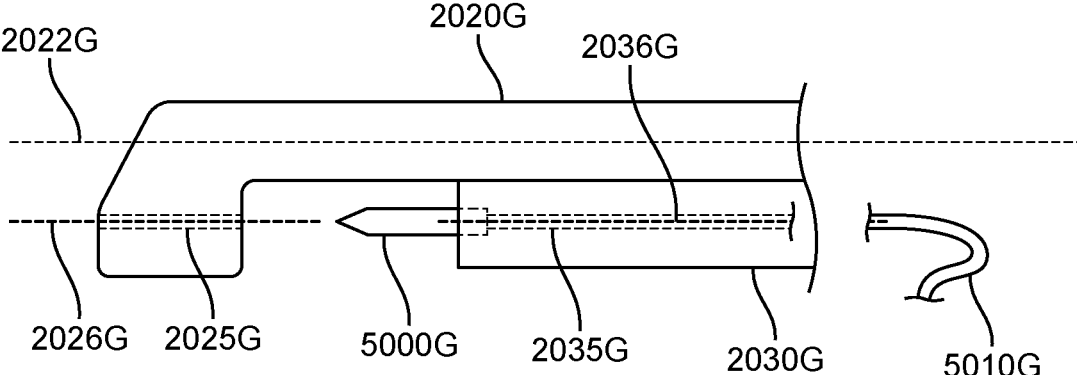

FIGS. 18A and 18B illustrate aspects of a suture device, according to embodiments of the present invention.

Figures 19A, 19B:
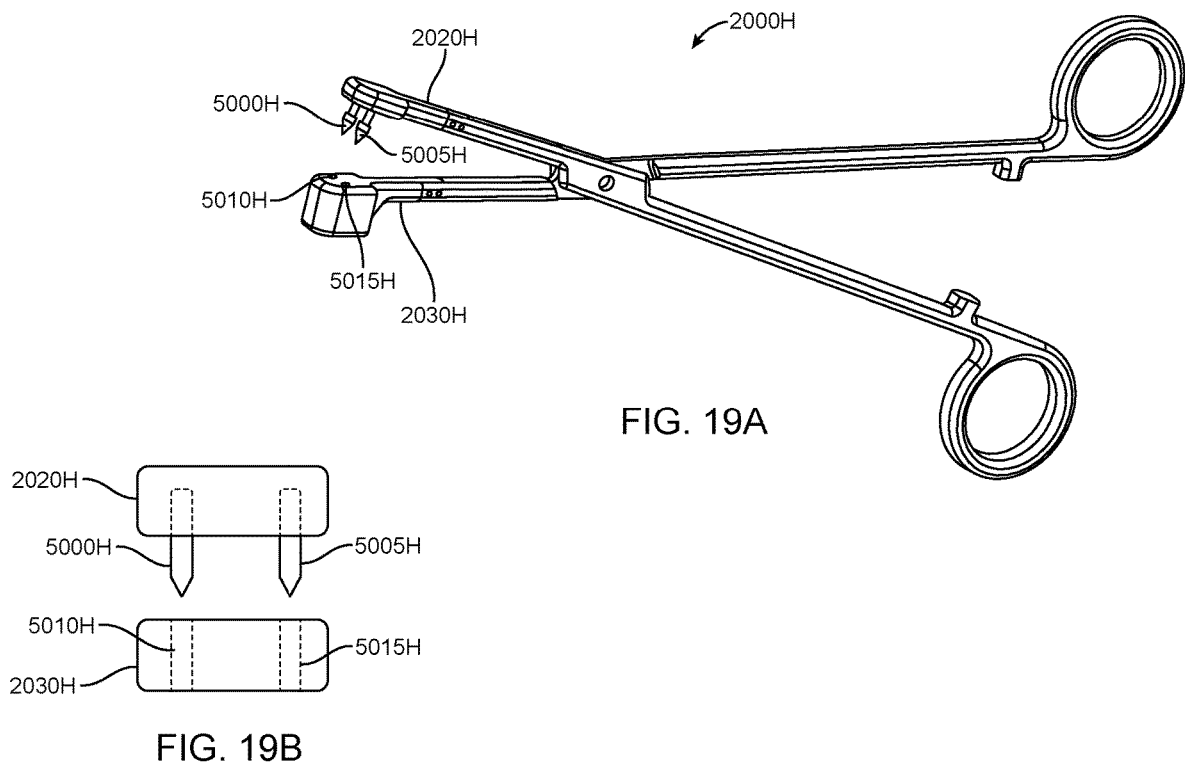

FIGS. 19A and 19B illustrate aspects of a suture device, according to embodiments of the present invention.

Figure 20A:
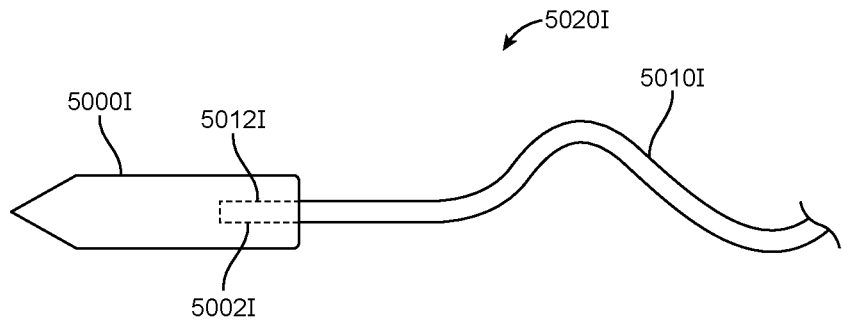
Figure 20B:
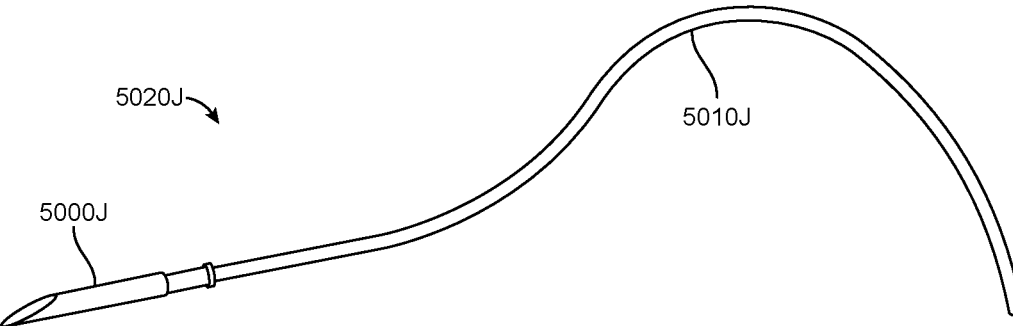

FIGS. 20A and 20B depict aspects of suture device needle assemblies, according to embodiments of the present invention.

FIGS. 21A to 21D depict aspects of a suture device, according to embodiments of the present invention.

Figure 22:
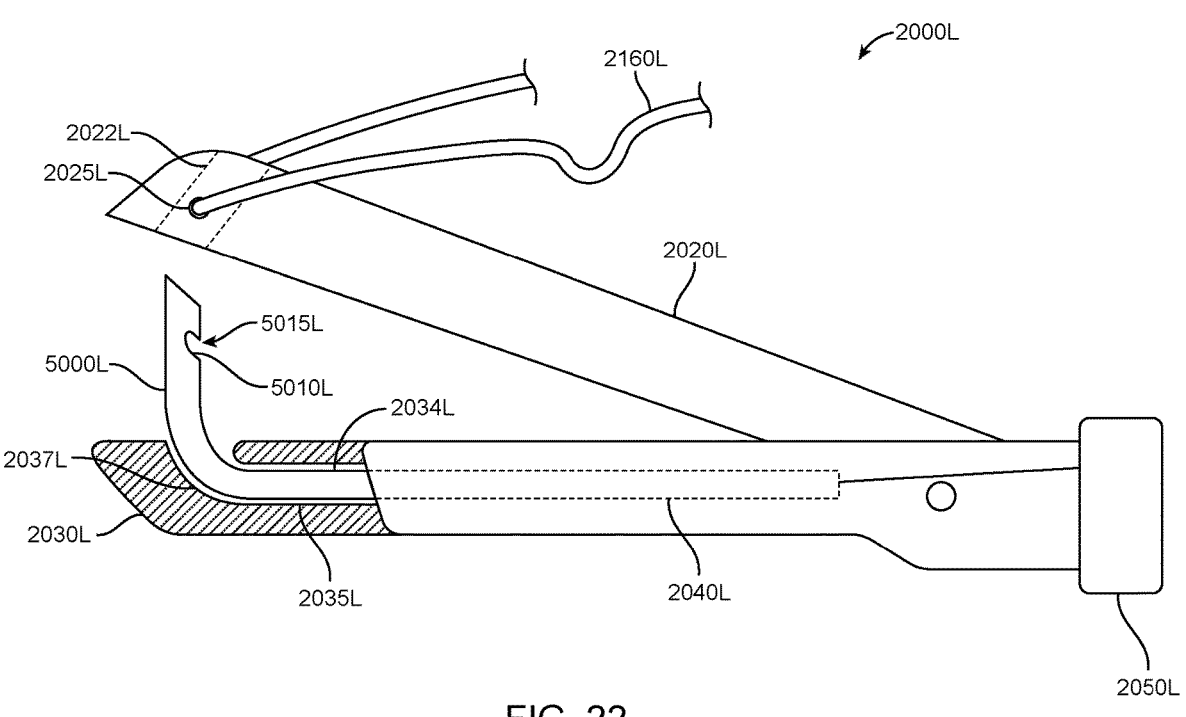

FIG. 22 illustrates aspects of a distal portion of a suture device, according to embodiments of the present invention.

FIGS. 23A to 23I depict aspects of suture devices, according to embodiments of the present invention.

FIGS. 24A to 24F depict aspects of a suture device, according to embodiments of the present invention.

Figures 25A, 25B:
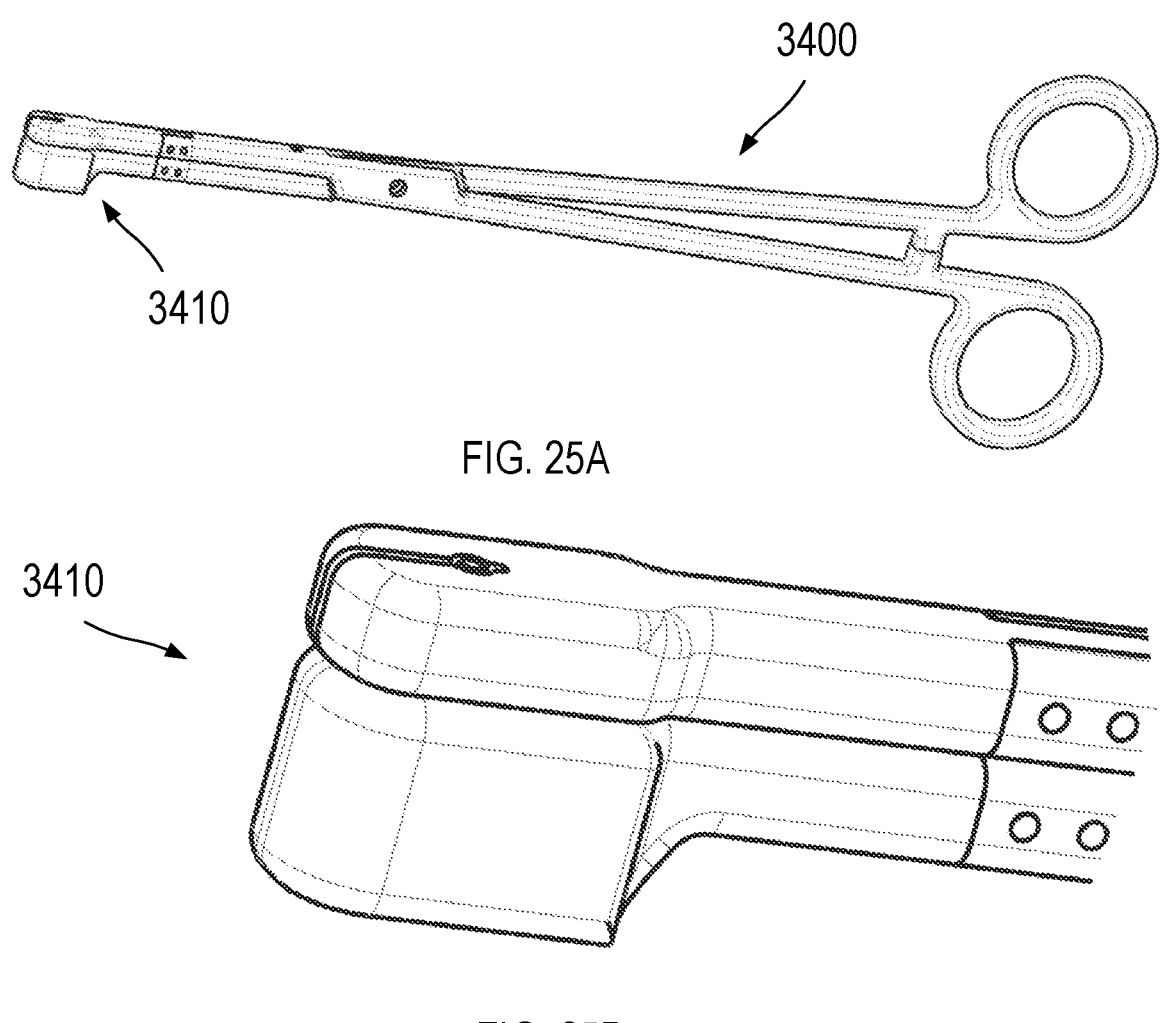

FIGS. 25A and 25B illustrate aspects of a suture device, according to embodiments of the present invention.

DETAILED DESCRIPTION OF THE INVENTION

All illustrations of the drawings are to describe selected embodiments of the present invention and are not intended to limit the scope of the present invention. Component parts shown in the drawings are not necessarily to scale, and may be exaggerated to better illustrate the important features of the present disclosure. References to user or users encompass either individual or individuals who would utilize embodiments of the present invention, and include surgeons, operators, and the like. Directional or positional references (e.g., proximal, distal, upper, lower, upward, downward, left, right, lateral, longitudinal, front, back, top, bottom, above, below, vertical, horizontal, radial, axial, clockwise, counterclockwise, and the like) are used for identification purposes to aid the reader's understanding of the present devices, systems, and structures described herein, and do not create limitations, particularly as to the position, orientation, or use of embodiments of the invention. In some cases, such references may be used interchangeably with other terms such as first, second, and the like. So for example upper and lower handles may be referred to as first and second handles, and vice versa. Connection references (e.g., attached, coupled, connected, joined, and the like) may be construed broadly and may include intermediate members between a collection of elements and relative movement between elements unless otherwise indicated.

The systems and methods described herein use a device to automatically retrieve a suture. The device described herein is made from a surgical steel that is capable of being sterilized (e.g., using an autoclave). In some embodiments, one or more components of a device can include or be manufactured from polyetherimide (e.g. Ultem®) or other types of resterilizable plastics. In such cases, the use of EtO or peroxide sterilization may be possible. Conventional devices are not indicated to be used more than once or resterilized, and they must be disposed of after use. The device described herein is also capable of being used with various types of sutures, including standard sutures commonly used in hospitals or surgical centers. Conventional devices may be limited to using a particular type of suture that is compatible with the mechanisms of the conventional devices. Thus, the systems and methods described herein are improvements to conventional devices for suturing, particularly in areas with limited visibility and space.

Figure 1:
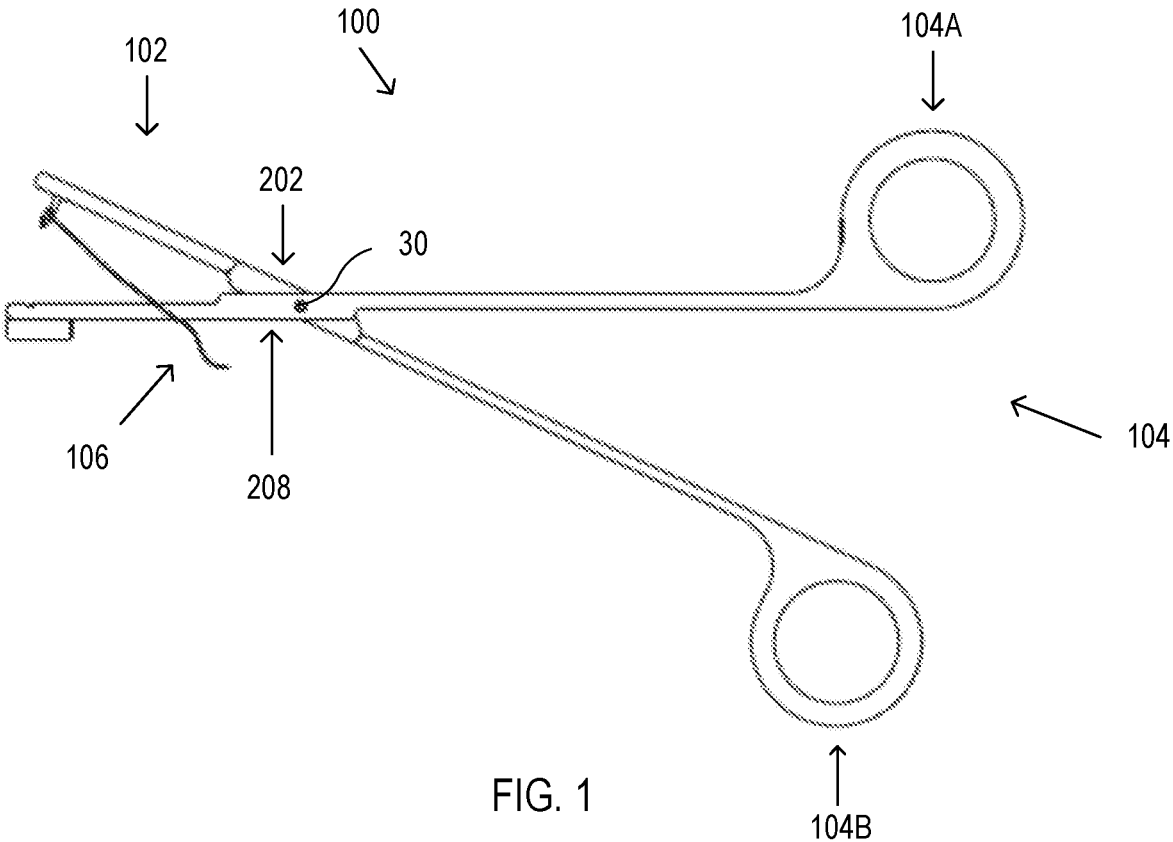
FIG. 1 depicts aspects of a suture device, according to embodiments of the present invention.

Turning now to the drawings, FIG. 1 illustrates an automatic suture retrieval device 100 in an open state. The device 100 has a distal end 102 and a proximal end 104. A head of the device 100 may be located on the distal end 102 and a handle for inserting fingers may be located on the proximal end 104. The device 100 may be manipulated in a similar manner as scissors. Using the device 100, a suture 106 such as a thread may be placed and automatically retrieved. The bottom handle 208 and the top handle 202 can be pivotably connected by a connector 30 and the distal ends of the bottom handle and the top handle can be moved toward each other to move the device to the closed position, and the distal ends of the bottom handle and the top handle can be moved away from each other to move the device to the open position.

The distal end 102 of the device can include an aperture that is configured to receive a needle, and the proximal end 104 can include a first or top finger ring 104A and a second or bottom finger ring 104B. The connector 30 can include a hinge, and the hinge can be disposed at a position or length between the distal end 102 and the proximal end 104, and can enable relative pivoting movement between the top handle 202 and the bottom handle 208.

Figure 2A:
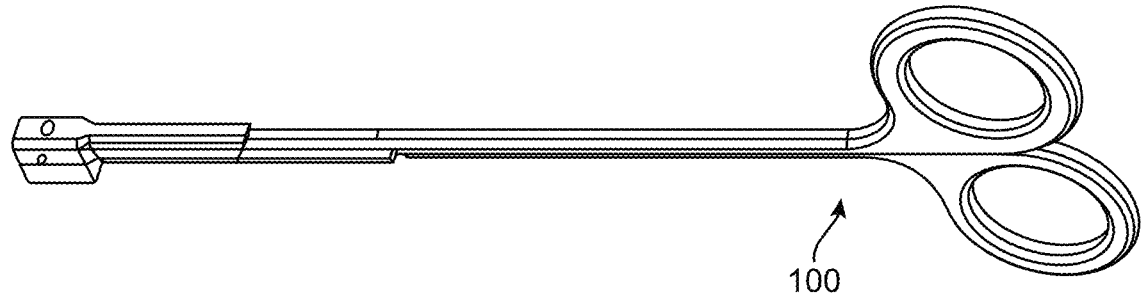
FIGS. 2A and 2B depict aspects of a suture device, according to embodiments of the present invention.
Figure 2B:
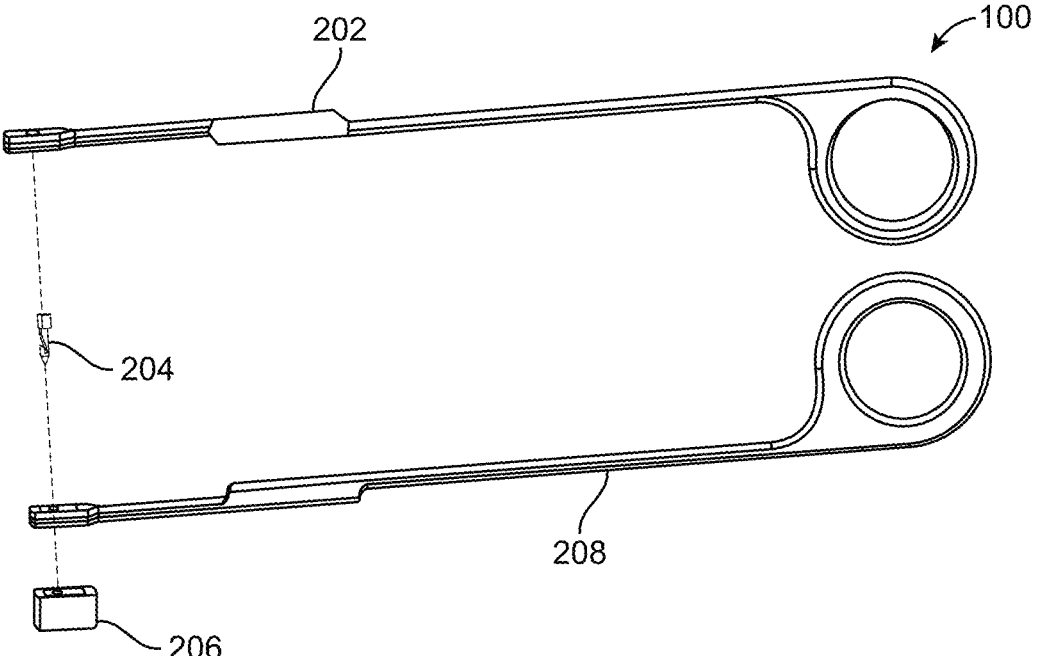

FIG. 2A provides an isometric view of device 100. FIG. 2B illustrates an exploded view of the automatic suture retrieval device 100. The device 100 includes a top handle 202, a bottom handle 208, a needle 204, and a base insert 206. The top handle 202 and the bottom handle 208 may be coupled together by a connector at a hinge that allows for pivoting movement of the top handle 202 relative to the bottom handle 208. The needle 204 is attached to the top handle 202 (e.g., using solder, an adhesive, welding, interference fit). In some embodiments, one or more needles of a device can be replaced from time to time. The base insert 206 is attached to the bottom handle 208 (e.g., using solder, an adhesive, welding, interference fit). In some embodiments, the base insert could also be removable from or removably attached with the bottom handle, via for example an engagement mechanism, a slip fit, or the like.

Figure 3:
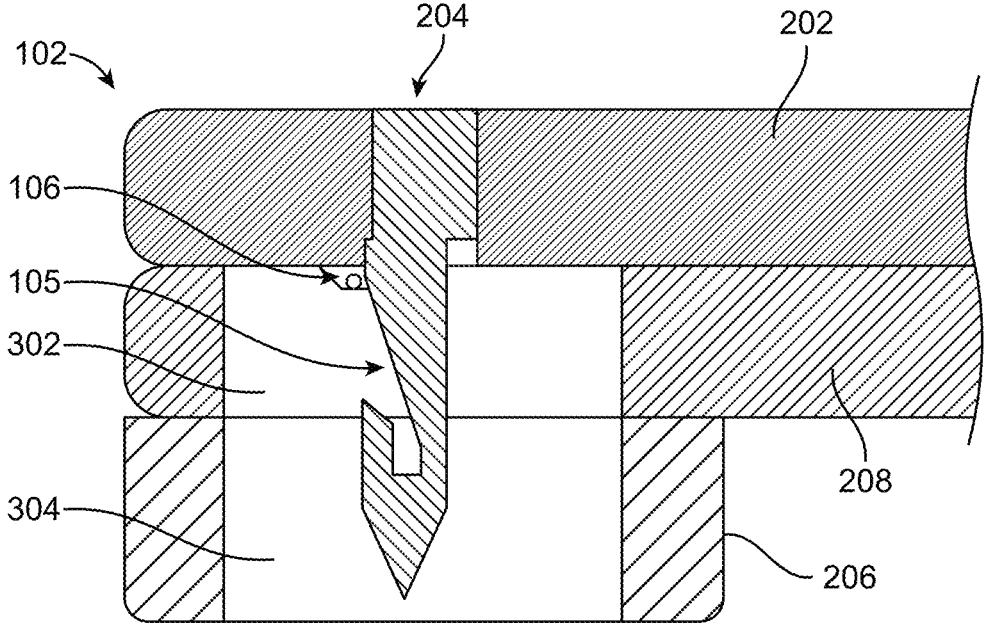
FIG. 3 illustrates aspects of a distal portion of a suture device, according to embodiments of the present invention.

FIG. 3 illustrates the distal end 102 of the automatic suture retrieval device 100 in a closed state. The device may be moved between the open state (shown in FIG. 1) and the closed state (shown in FIG. 3) by the fingers of the user being separated or brought together.

As shown in FIG. 3, when the device 100 is in the closed state, the needle 204 passes through an opening of the bottom handle 208 and into the base insert 206. That is, the needle 204 is received by a cavity 302 of the bottom handle 208 and a cavity 304 of the base insert 206.

The suture 106 may be received and retained by a channel of the bottom handle 208, as further shown herein. In some embodiments, device 100 is a device for threading and automatically retrieving a suture, and includes a bottom handle 208 with a cavity 302 for receiving and retaining a suture, and a top handle 202 that is coupled with a needle 204. The needle can have an opening 105 that is configured to receive and retrieve a suture 106 as the device is moved from a closed position to an open position. As shown here, the bottom handle 208 includes an aperture or cavity 302 for receiving the needle 204 when the device is in the closed position, and a channel can hold the suture 106 across the aperture 302.

FIG. 4A provides an isometric view of the top handle 202. As shown in the side view of FIG. 4B, the top handle 202 has a distal end 404 and a proximal end 406. As shown in the bottom view of FIG. 4C, the distal end 404 includes an aperture 402 for receiving the needle 204. As shown in the magnified partial bottom view of FIG. 4D, the aperture 402 includes a flat portion 402*f* and a curved portion 402*c*.

FIG. 5A provides an isometric view of needle 204. As shown in the rear view of FIG. 5B and the side view of FIG. 5C, the needle 204 includes an attachment portion 510, a body portion 508, and a tip portion 502. The tip portion 502 pierces a tissue of the patient and creates a space for the body portion 508 to pass through the tissue.

With returning reference to FIG. 4D, the attachment portion 510 is received by the aperture 402 of the top handle 202 and may be attached to the top handle 202. For example, a flat portion 510*f* and curved portion 510*c* of the attachment portion of the needle 204 can engage or interface with the flat portion 402*f* and the curved portion 402*c*, respectively, of the aperture 402. As shown in FIG. 5C, the body portion 508 includes an opening 504 for receiving and retrieving the suture 106 as the device 100 is moved to the open state. The body portion 508 includes an inclined edge 506 that guides the suture through the opening 504. FIG. 5D depicts a partial view of body portion 508, where the suture 106 (cross-section) is positioned in a bottom portion 507 of the opening 504. In some cases, the inclined edge includes at least one side that has a sharp edge. In some cases, the inclined edge includes two sides each having a sharp edge. In some cases, a tip of the needle has a sharp edge.

FIG. 6A provides an isometric view of the bottom handle 208. As shown in the side view of FIG. 6B, the bottom handle 208 has a distal end 604 and a proximal end 606. As shown in the magnified side view of FIG. 6C, the distal end 604 includes a channel 602 for receiving and retaining the suture 106 prior to the suturing of the suture 106. In some cases, channel 602 is configured to receive any suture, including for example a tape suture. In some cases, channel 602 is configured to receive multiple sutures. As shown in the top view of FIG. 6D and the magnified top view of FIG. 6E, the distal end 604 also includes an aperture 610 that defines the cavity 302 shown in FIG. 3.

FIG. 7 illustrates a side cross-sectional view of the distal end 102 of the automatic suture retrieval device 100 in the closed position, with suture 106 held by the channel 602 of the bottom handle 208. In some embodiments, the base insert 206 has four side walls that define a cavity 304. In some embodiments, the base insert 206 also includes a bottom wall, and in other embodiments, the base insert 206 only includes only four side walls. In some embodiments, device 100 is a device for threading and automatically retrieving a suture, and includes a bottom handle 208 with a channel or cavity for receiving and retaining a suture 106, and a top handle 202 that is coupled with a needle. The needle can have an opening that is configured to receive and retrieve a suture 106 as the device is moved from a closed position to an open position. As shown here, the bottom handle 208 includes an aperture or cavity 302 for receiving the needle when the device is in the closed position, and a channel 602 can hold the suture 106 across the aperture 302.

FIGS. 8A to 8G illustrate a sequence of steps of using the automatic suture retrieval device 100 for threading the suture 106 through a tissue 1002 and retrieving the suture 106. The tissue 1002 may be any body tissue of a patient. In some embodiments, the device 100 may be used to insert any thread through a material and automatically retrieve the thread.

Figure 8A:
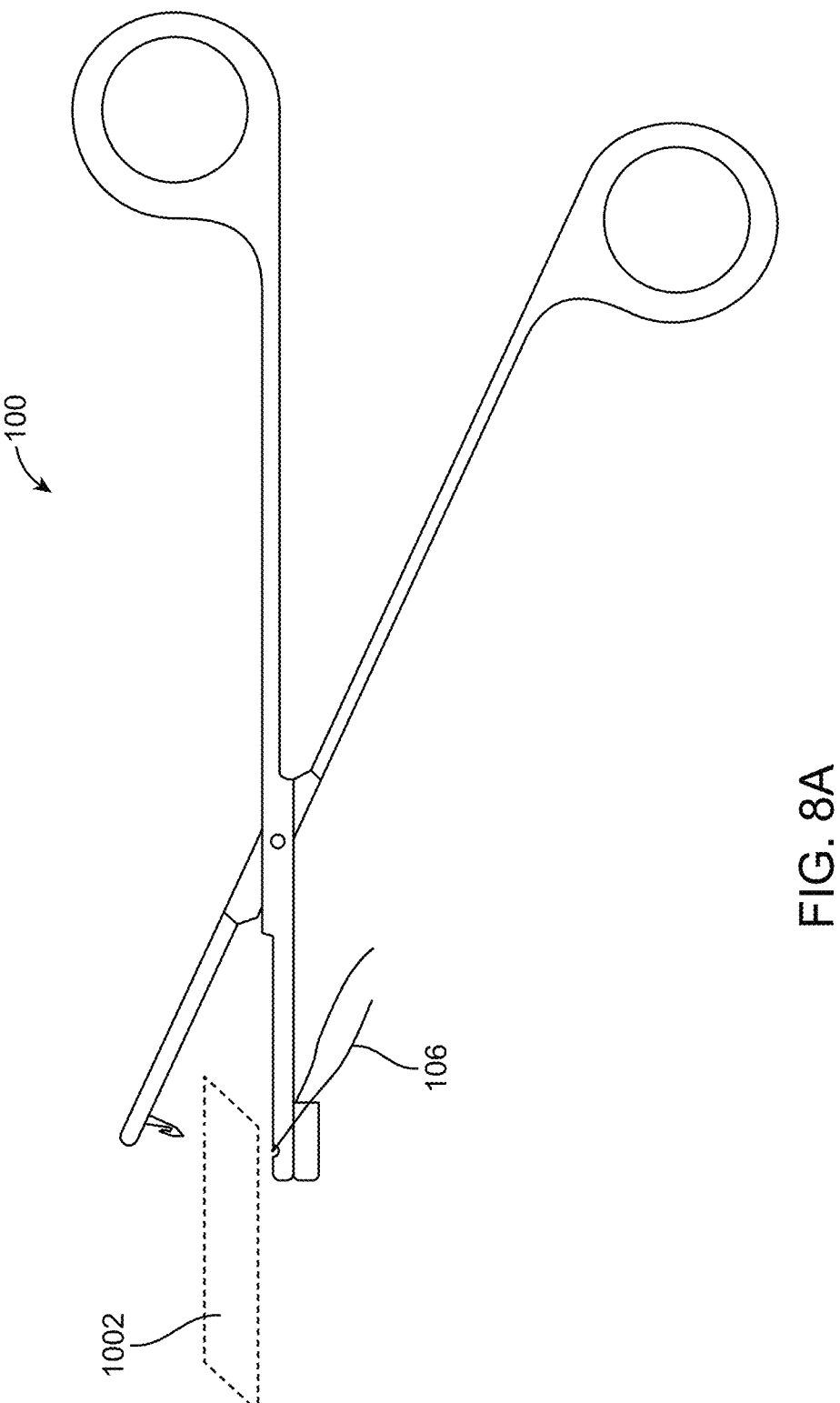
Figure 8B:
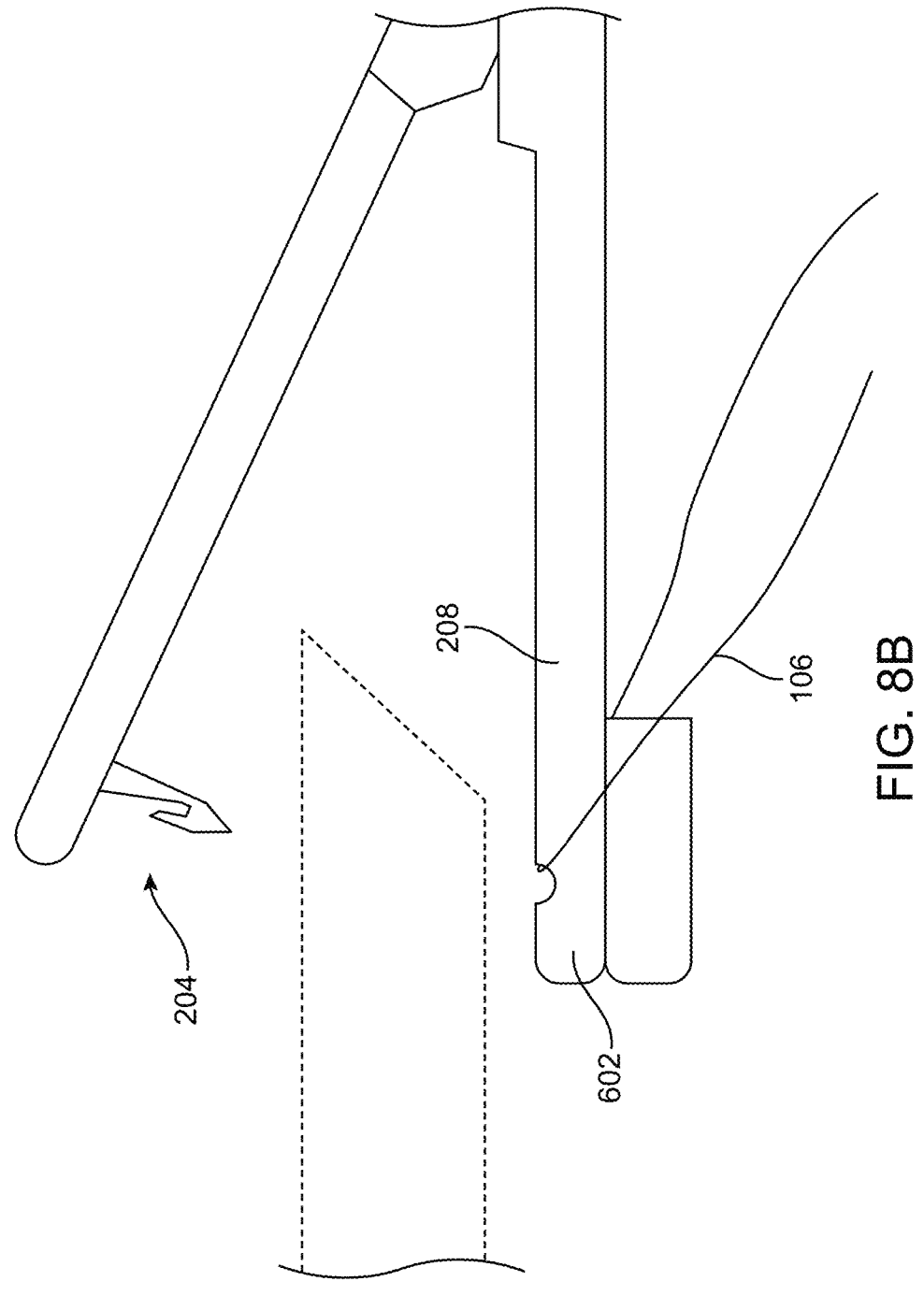

As shown in FIGS. 8A and 8B, the automatic suture retrieval device 100 is in the open position with the suture 106 held and secured by the channel 602 of the bottom handle 208. The needle 204 is on an opposite side of the tissue 1002 as the suture 106.

While the suture 106 is illustrated here as having slack, the suture 106 may be held taut to maintain its position within the channel 602 of the bottom handle 208. The suture 106 may be held taut by the user (e.g., a surgeon) or may be held taut using another mechanism or device. In exemplary embodiments, the tension on the suture to hold the suture taut may be easily overcome by the device 100 when the device 100 moves from the closed position to the open position, so that the suture may be retrieved through the tissue.

Figure 8C:
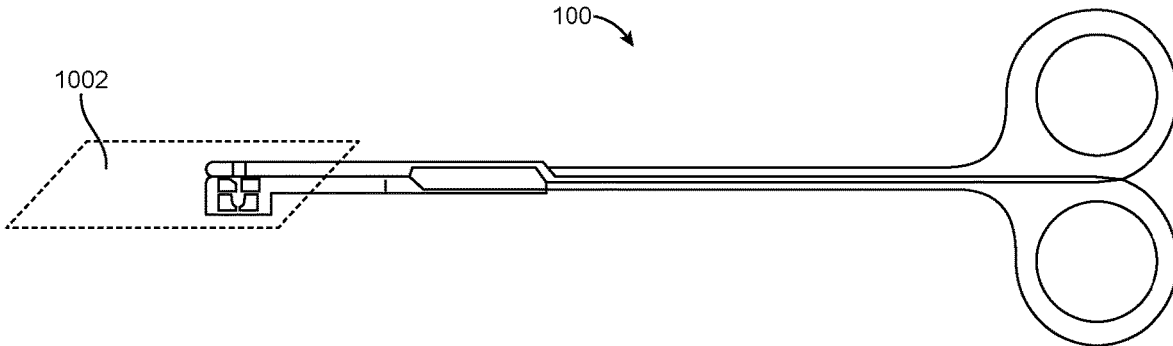
Figure 8D:
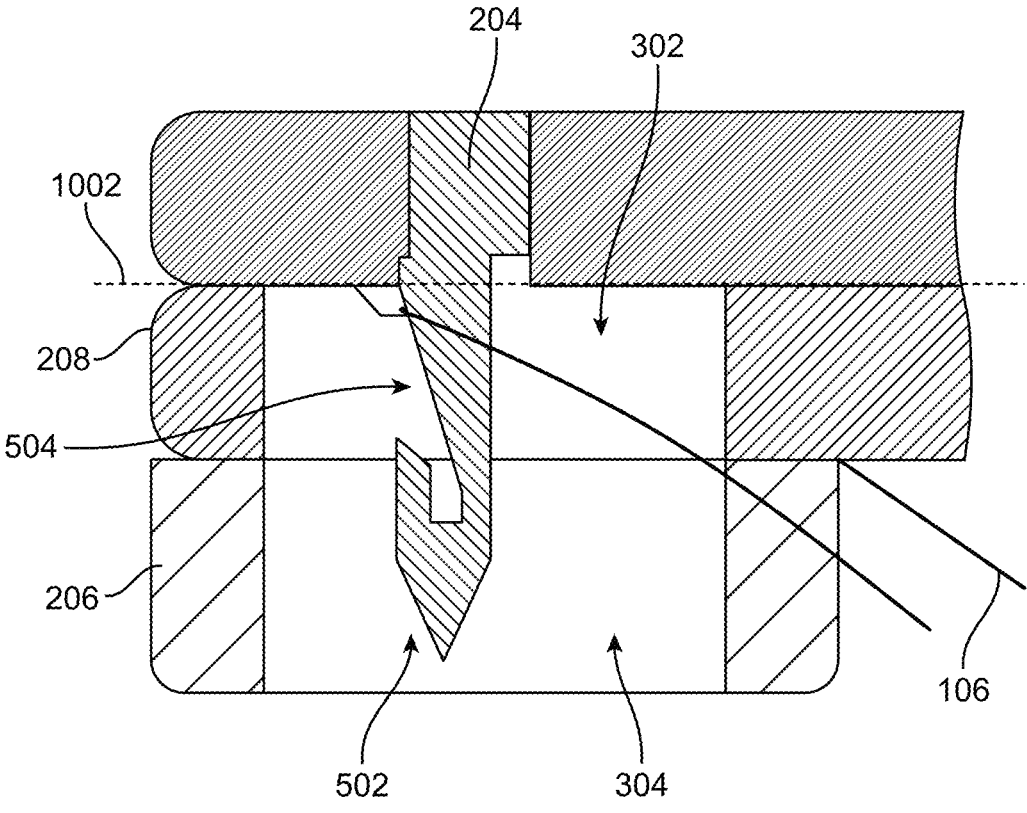

FIGS. 8C and 8D illustrate the automatic suture retrieval device 100 in the closed position around the tissue 1002. The automatic suture retrieval device 100 may be moved to the closed position by the user moving the user's fingers together while engaged with the handle of the device 100.

As shown in FIG. 8D, the needle 204 has penetrated the tissue 1002. The tip portion 502 of the needle 204 has pierced the tissue 1002 and created an opening for the body portion of the needle 204 to pass through the tissue 1002. The needle 204 passes by the suture 106 held in place by the channel 602 and is now within the cavities 302, 304 of the bottom handle 208 and the base insert 206, respectively. The opening 504 of the needle 204 is now on the same side of the tissue 1002 as the suture 106. In some embodiments, device 100 is a device for threading and automatically retrieving a suture, and includes a bottom handle 208 with a channel for receiving and retaining a suture 106, and a top handle that is coupled with a needle 204. The needle can have an opening 504 that is configured to receive and retrieve a suture 106 as the device is moved from a closed position to an open position.

Hence, it can be seen that method embodiments of the present invention can encompass process steps such as disposing the suture 106 across a channel of the bottom handle 208, clasping a distal end of the device onto a tissue 1002 by moving the device from an open position to a closed position, whereby the clasping causes the needle 204 to pierce the tissue 1002. As further discussed elsewhere herein, methods can also include unclasping the distal end of the device from the tissue 1002 by moving the device from the closed position to the open position, whereby the unclasping causes the opening 504 of the needle 204 to receive and retrieve the suture 106 through the tissue 1002.

Figure 8E:
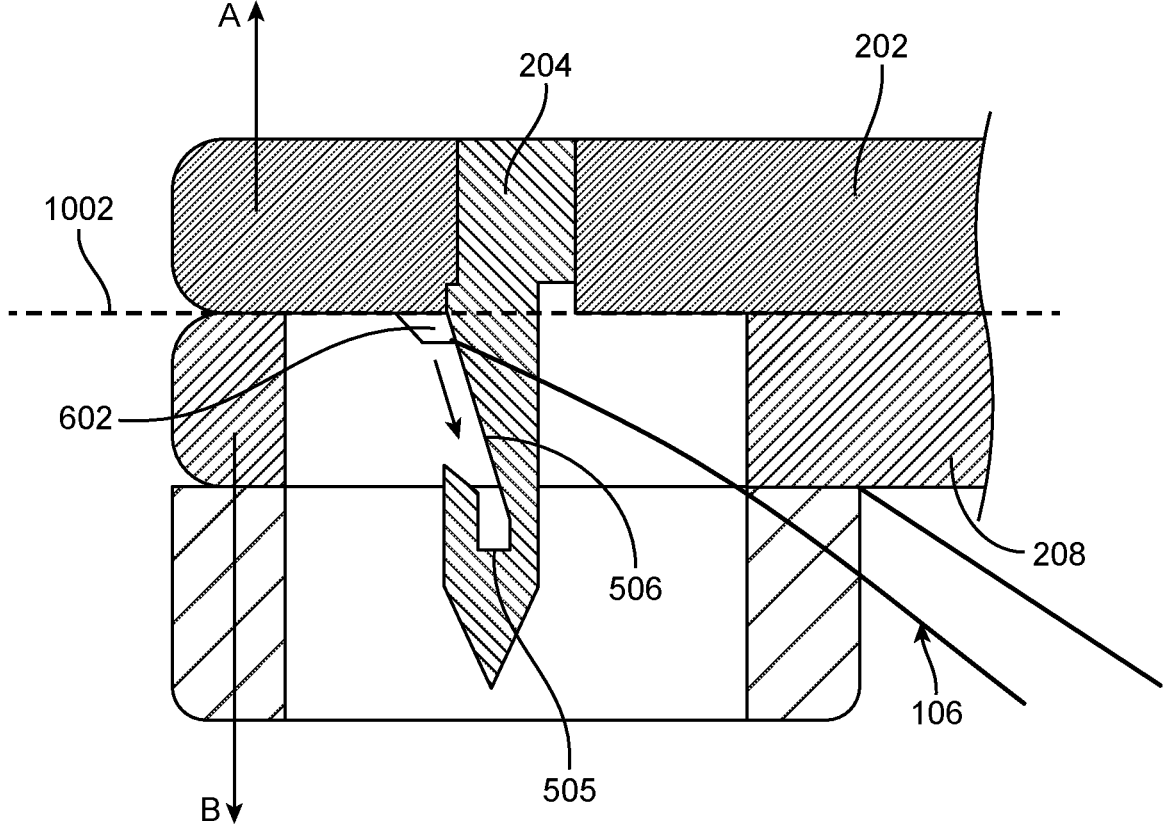

FIG. 8E illustrates aspects of the retrieval of the suture 106 using the needle 204. As shown here, the bottom handle 208 includes an aperture or cavity for receiving the needle

204 when the device is in the closed position, and a channel 602 can hold the suture 106 across the aperture 302. As the automatic suture retrieval device 100 is moved from the closed position to the open position, the top handle 202 and the bottom handle 208 move away from each other as indicated by arrows A and B. Accordingly, the suture 106 is received by the opening 504 of the needle 204 and the suture 106 slides down the inclined edge 506 of the needle 204. The suture 106 is secured by a bottom surface 505 of the opening 504 of the needle 204.

Figure 8F:
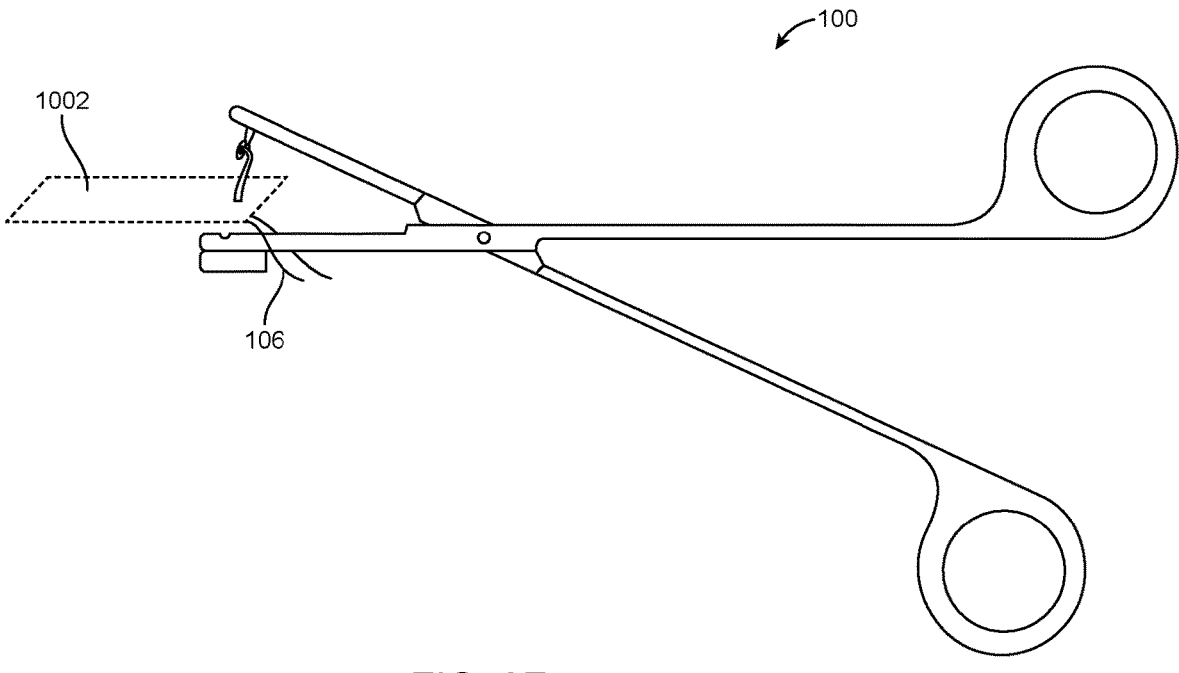
Figure 8G:
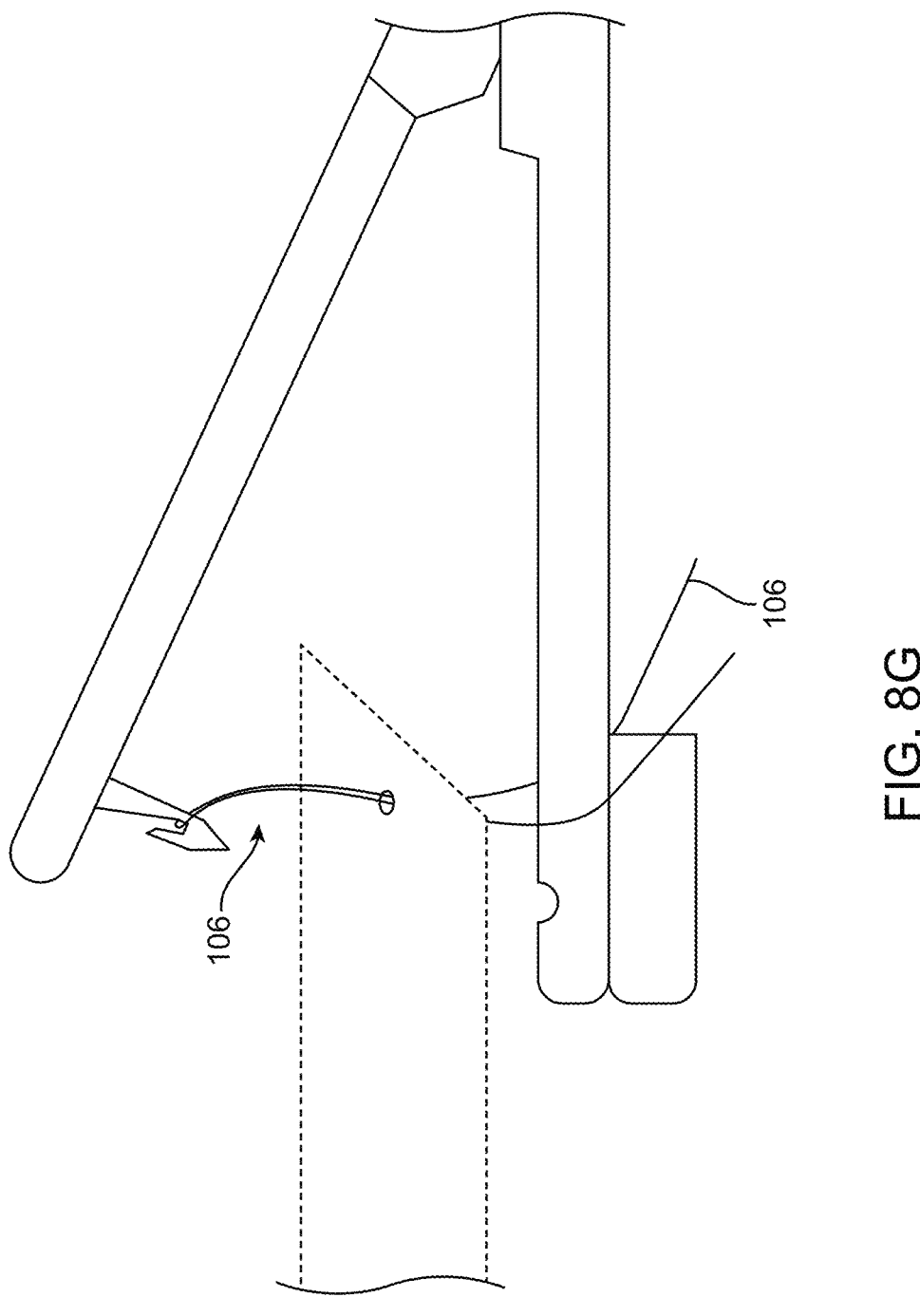

FIGS. 8F and 8G illustrate the automatic suture retrieval device 100 in the open position. The suture 106 passes through the tissue 1002. The device 100 may then be maneuvered by the user to perform the remaining steps of the surgical procedure.

As disclosed herein, the automatic suture retrieval device 100 allows for the threading and retrieval of suture 106 through tissue 1002 in situations where there is limited visibility and space. In addition, the design of the device 100 allows for cost-effective manufacture. The device 100 can be configured to be sterilized for re-use, and can also be compatible with any suture 106. In some cases, the device can be compatible for use with suture tape.

FIGS. 9A and 9B illustrate an embodiment of an automatic suture device 2000 in a closed state and an open state. FIG. 9A illustrates the automatic suture device 2000 in a closed state. The device has a distal end 2010 and a proximal end 2020, and contains a connector 2030 at a hinge that allows for pivoting movement of the top handle 2032 and the bottom handle 2034 relative to one another. At the distal end, there is a base insert 2035 capable of receiving a needle. FIG. 9B illustrates the automatic suture device 2000 in an open state, which illustrates the connector 2030, as well as the main top jaw 2040, the main bottom jaw 2050, and the needle 2060. FIG. 9C illustrates the top handle 2032 of the automatic suture device. The top handle contains a proximal end 2080 and a distal end 2090. The distal end contains an aperture 3000 for receiving a needle. The bottom handle 2034 and the top handle 2032 can be pivotably connected by a connector 2030 and the distal ends of the bottom handle and the top handle can be moved toward each other to move the device to the closed position, and the distal ends of the bottom handle and the top handle can be moved away from each other to move the device to the open position.

FIG. 10 illustrates different aspects of a top handle 3005 of an automatic suture device. The device has a distal end 3010 and a proximal end 3020, and contains a connector 3030 at a hinge that allows for pivoting movement of the handles. At the distal end, the device contains an aperture for receiving a needle. The device contains a shank 3050 with a length between the connector 3030 and the proximal end 3020.

FIGS. 11A and 11B illustrate different aspects and different partial views of a top handle 4005 of an automatic suture device. The device has a distal end 4000 and a proximal end, and contains a connector 4020 at a hinge that allows for pivoting movement of the handles. The device contains an aperture 4030 for receiving a needle.

FIGS. 12A and 12B illustrate an embodiment of a needle 5000. As shown in FIG. 12A, the needle 5000 contains an attachment portion 5010, a body portion 5020, and a tip portion 5030. The needle 5000 contains an opening 5040 that guides a suture to an inclined edge 5050. The suture slides down the inclined edge. The suture is secured by a surface of the opening. FIG. 12B provides a partial side view of needle 5000. As shown here, a needle 5000 can include an attachment portion 5010 that is configured to be received by an aperture of a handle of a suture device, a tip portion 5030 that is configured to pierce a tissue of a patient, and a body portion 5020 that is configured to pass through the tissue that has been pierced by the tip portion. The body portion 5020 can include one or more openings, each opening 5040 having an inclined edge 5050 that guides a suture through the opening.

Figures 13D, 13E:
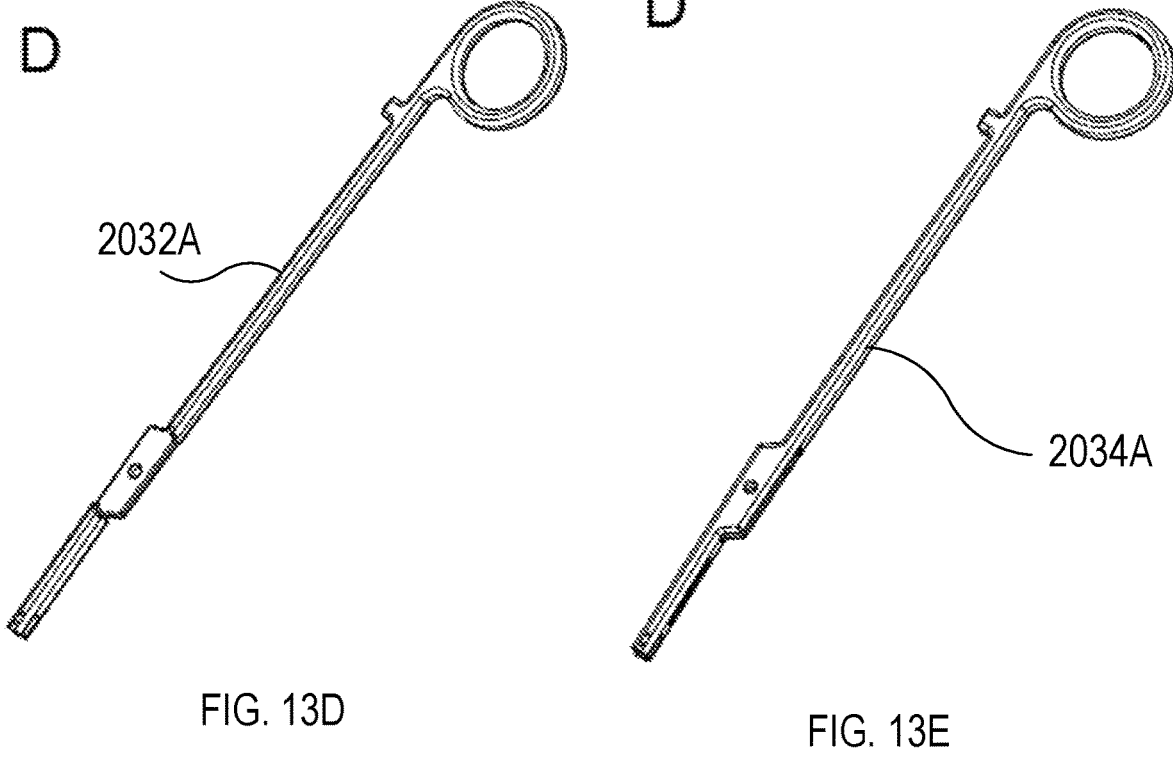
Figure 13F:
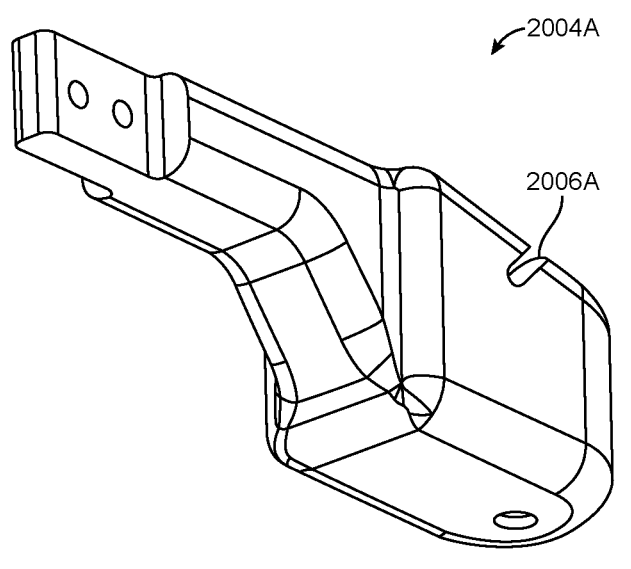
Figure 13G:
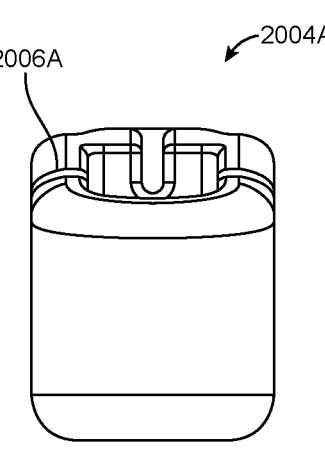
Figure 13H:
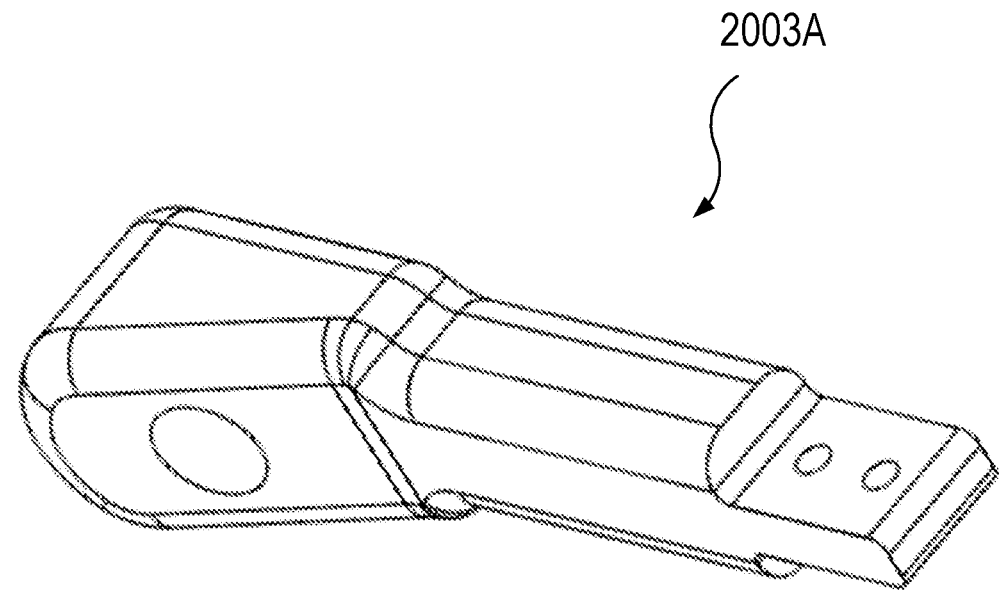
Figures 13I, 13J, 13K, 13L:
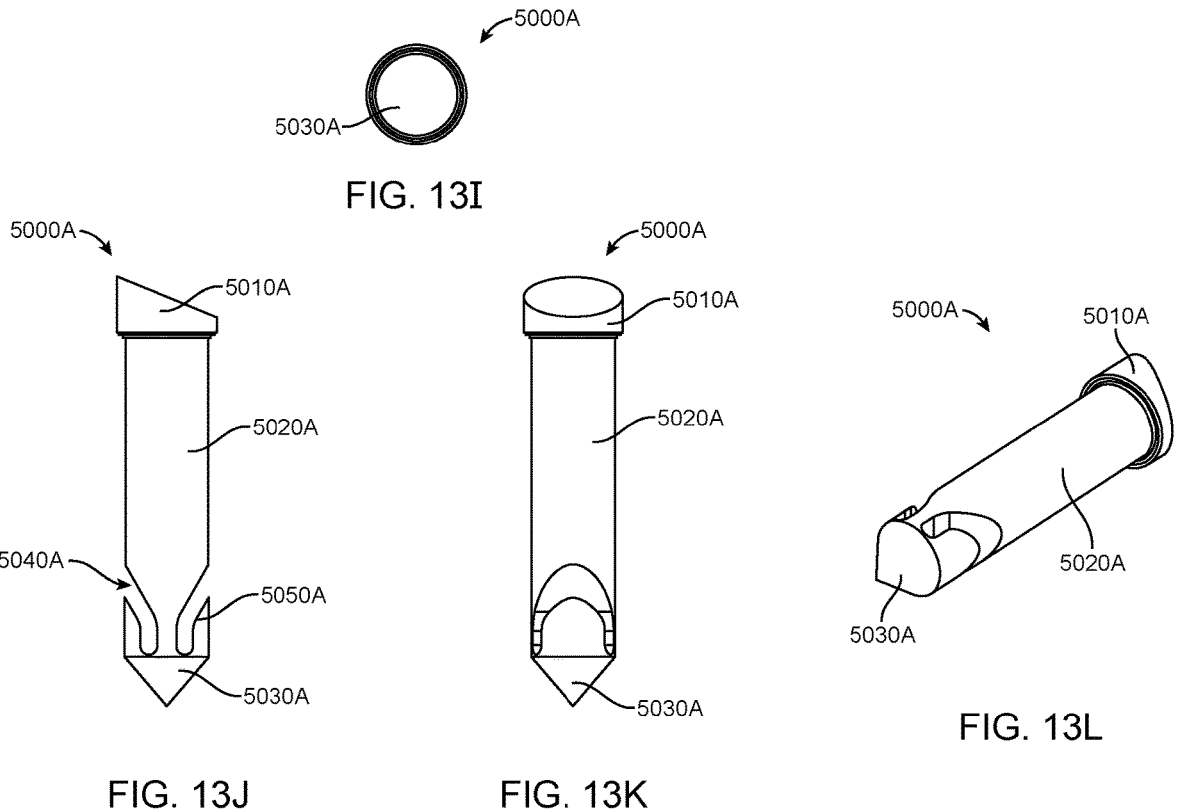

FIGS. 13A to 13L illustrate an embodiment of an automatic suture device 2000A in a closed state. As shown in FIGS. 13A to 13C, the device 2000A has a distal end 2010A and a proximal end 2020A. The device 2000A includes a connector 2030A at a hinge that allows for pivoting movement of the top handle 2034A and the bottom handle 2032A relative to one another. The bottom handle 2032A and the top handle 2034A can be pivotably connected by a connector 2030A and the distal ends of the bottom handle and the top handle can be moved toward each other to move the device to the closed position, and the distal ends of the bottom handle and the top handle can be moved away from each other to move the device to the open position. FIG. 13D depicts bottom handle 2032A and FIG. 13E depicts top handle 2034A. FIG. 13F provides a perspective view of a needle catcher 2004A and FIG. 13G provides an end view of needle catcher 2004A. As shown here, the needle catcher 2004A includes a channel 2006A. FIG. 13H provides a perspective view of a needle holder 2003A. FIGS. 13I to 13L depict different views of a needle 5000A of an automatic suture device. As shown here, needle 5000A includes an attachment portion 5010A, a body portion 5020A, and a tip portion 5030A. The needle 5000A contains one or more openings 5040A, each can operate to guide a suture to an inclined edge 5050A. The suture slides down the inclined edge. The suture is secured by a surface of the opening.

As shown here, a needle 5000A can include an attachment portion 5010A that is configured to be received by an aperture of a handle of a suture device, a tip portion 5030A that is configured to pierce a tissue of a patient, and a body portion 5020A that is configured to pass through the tissue that has been pierced by the tip portion. The body portion 5020A can include one or more openings, each opening 5040A having an inclined edge 5050A that guides a suture through the opening.

Figure 14A:
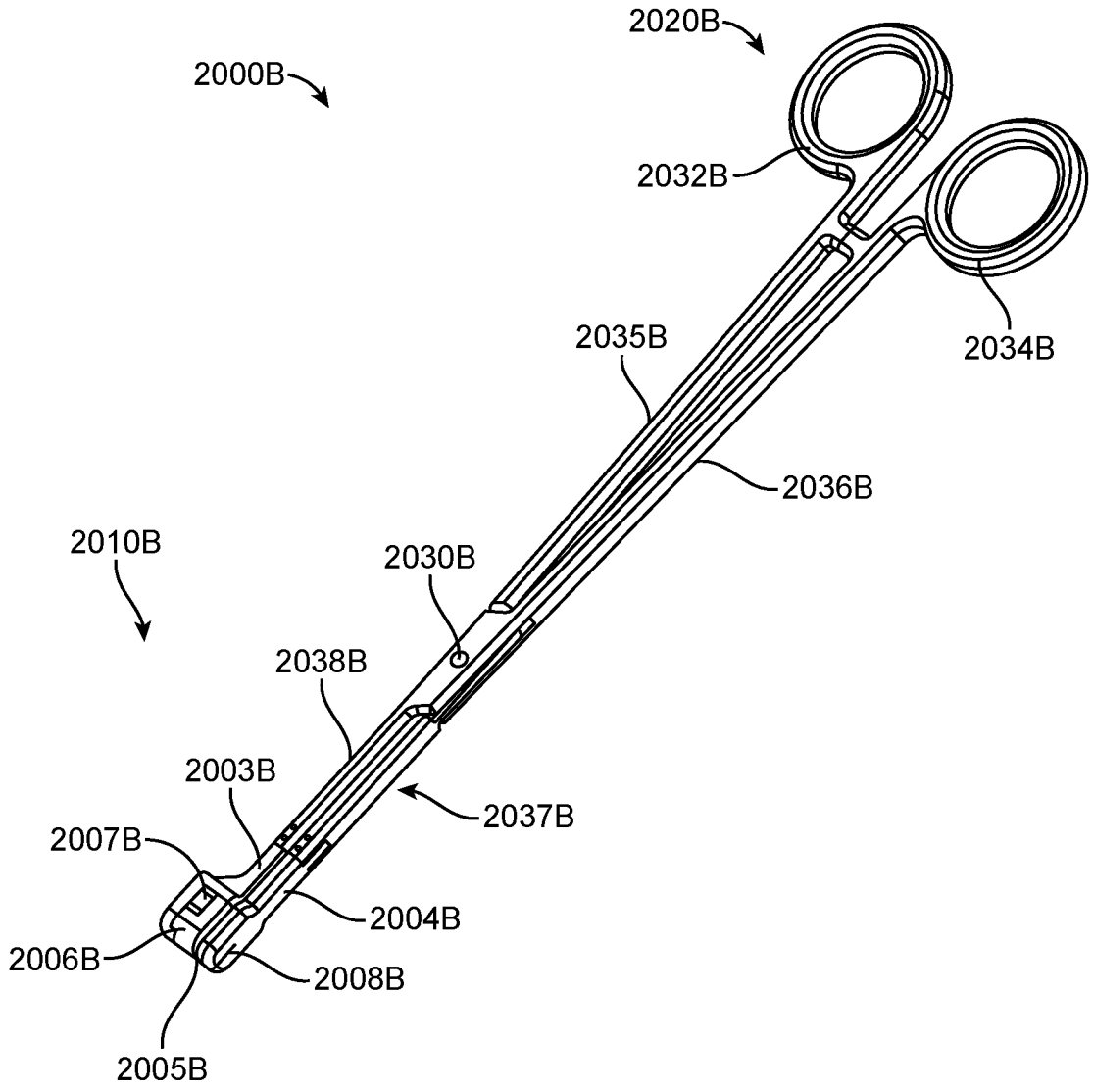

FIGS. 14A to 14D illustrate aspects of an embodiment of an automatic suture device 2000B in a closed state. As shown in FIG. 14A, the device 2000B has a distal end 2010B and a proximal end 2020B, and contains a connector 2030B at a hinge that allows for pivoting movement of a first handle 2034B (e.g. top handle) and a second handle 2032B (e.g. bottom handle) relative to one another. As shown here, the device 2000B includes a needle holder 2003B, a needle catcher 2004B, a left catcher 2005B, a right catcher 2006B, a center notch 2007B, and a needle 2008B. First handle 2034B can include a first shank 2036B and a first jaw 2038B. Second handle 2032B can include a second shank 2035B and a second jaw 2037B. The first handle 2034B and the second handle 2032B can be pivotably connected by a connector 2030B and the distal ends of the bottom handle and the top handle can be moved toward each other to move the device to the closed position, and the distal ends of the bottom handle and the top handle can be moved away from each other to move the device to the open position.

Figure 14B:
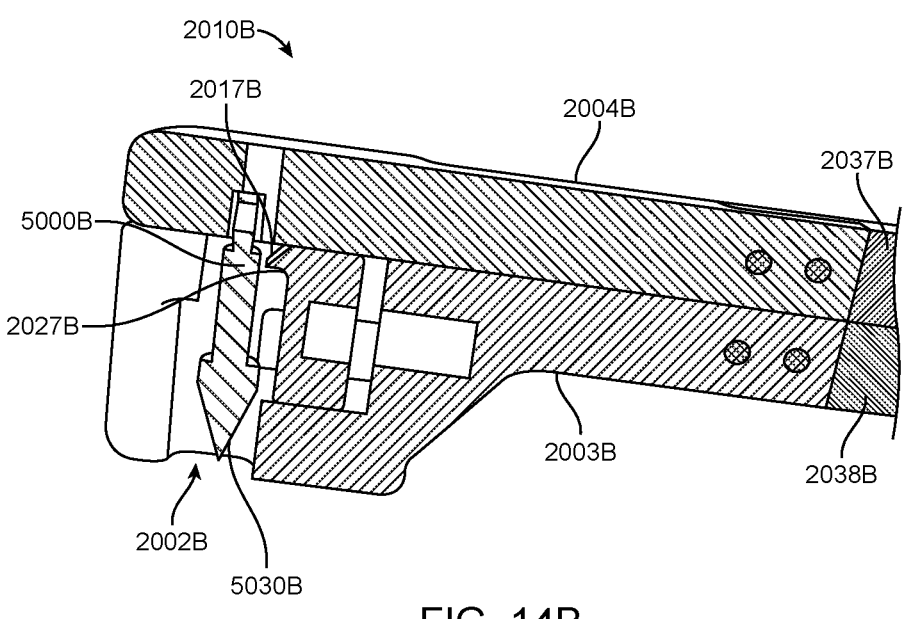
Figures 14C, 14D:
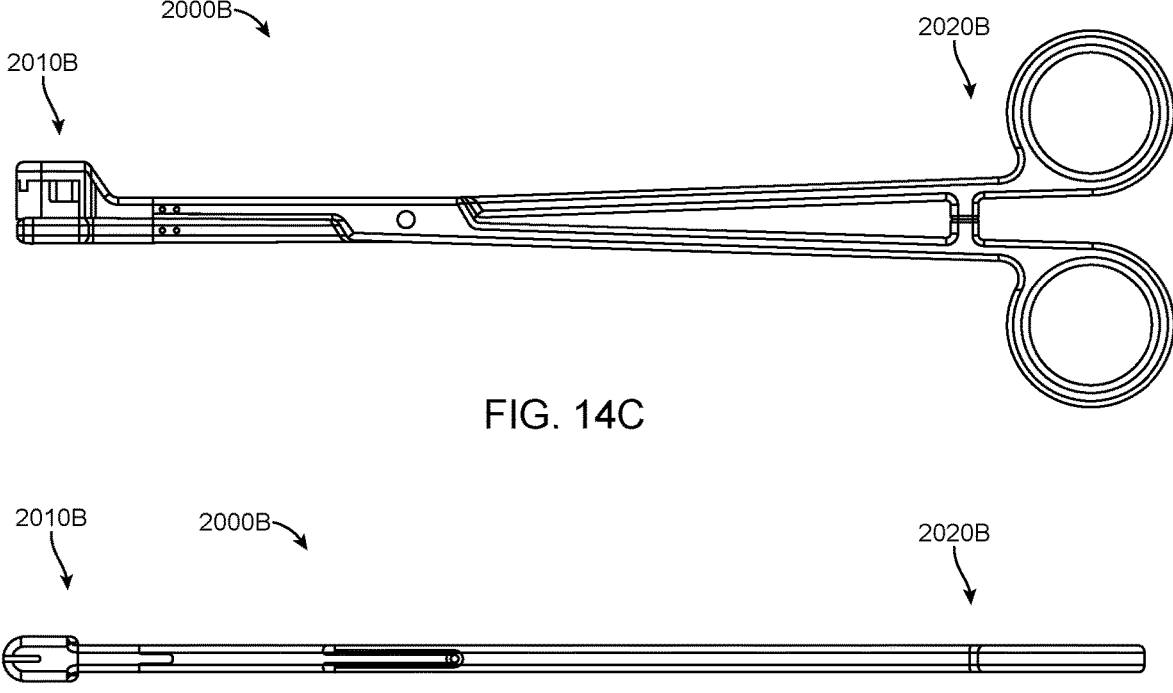

FIG. 14B provides a cross-section view of the distal end 2010B of the device. As shown here, first jaw 2038B is coupled with needle holder 2003B, and second jaw 2037B is coupled with needle catcher 2004B. Needle 5000B extends from needle catcher 2004B into a space or aperture 2002B of needle holder 2003B. FIG. 14C provides a side view of suture device 2000B and FIG. 14D provides a plan view of suture device 2000B.

Figure 14E:
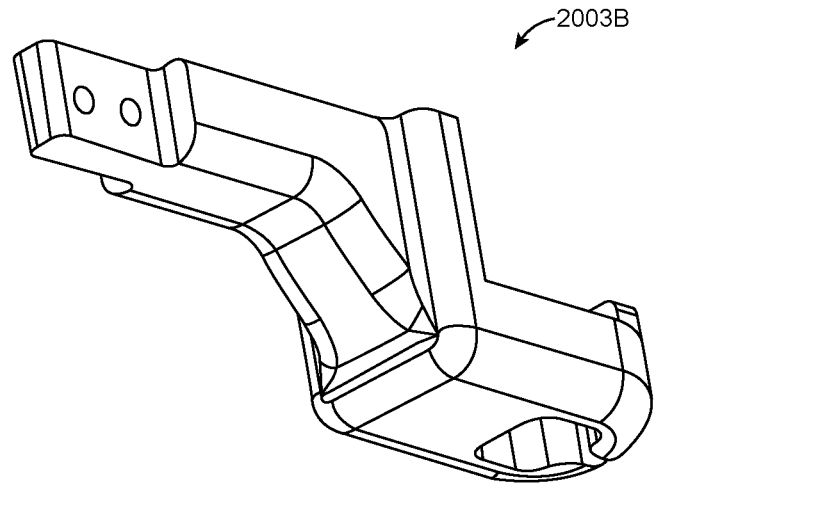
Figure 14F:
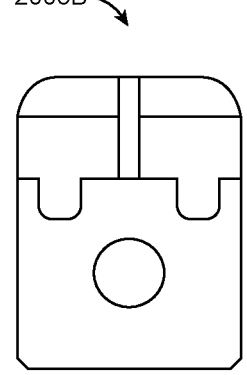
Figure 14G:
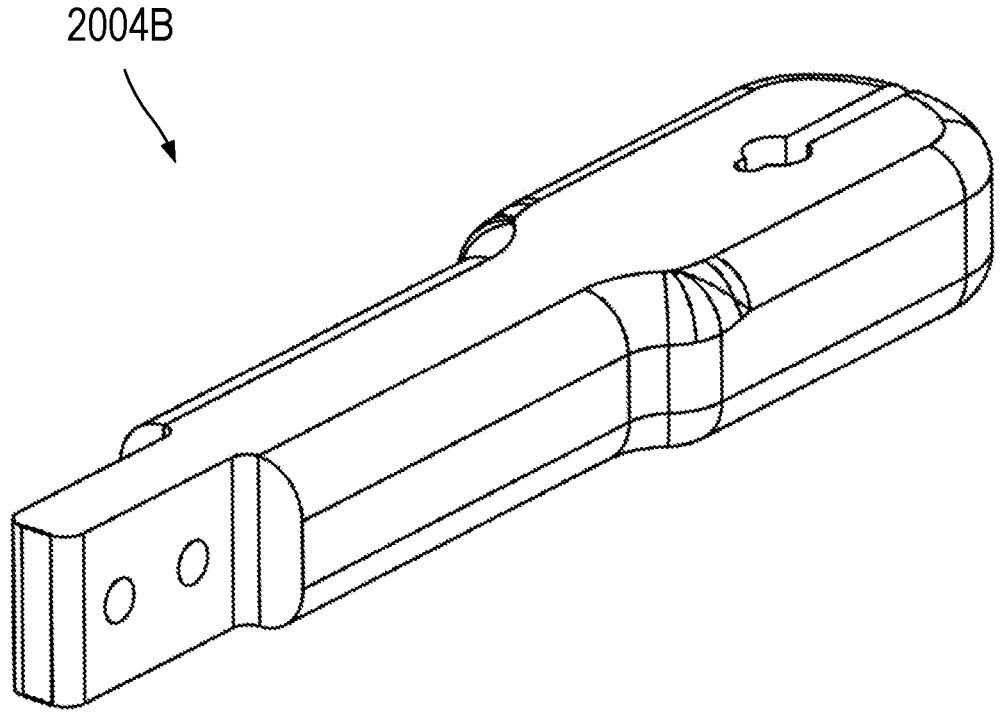
Figures 14G, 14H, 14I:
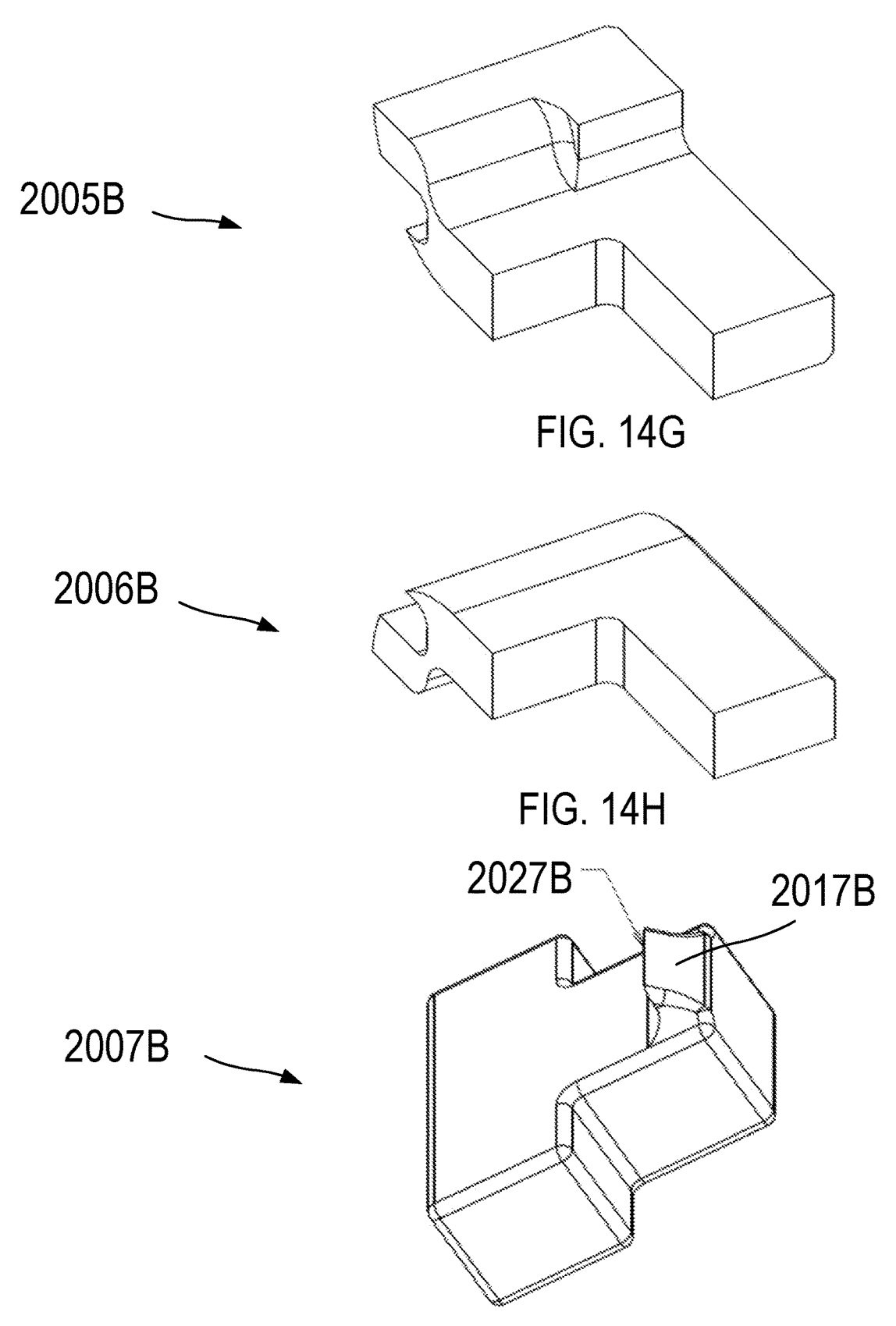
Figures 15A, 15B, 15C, 15D:
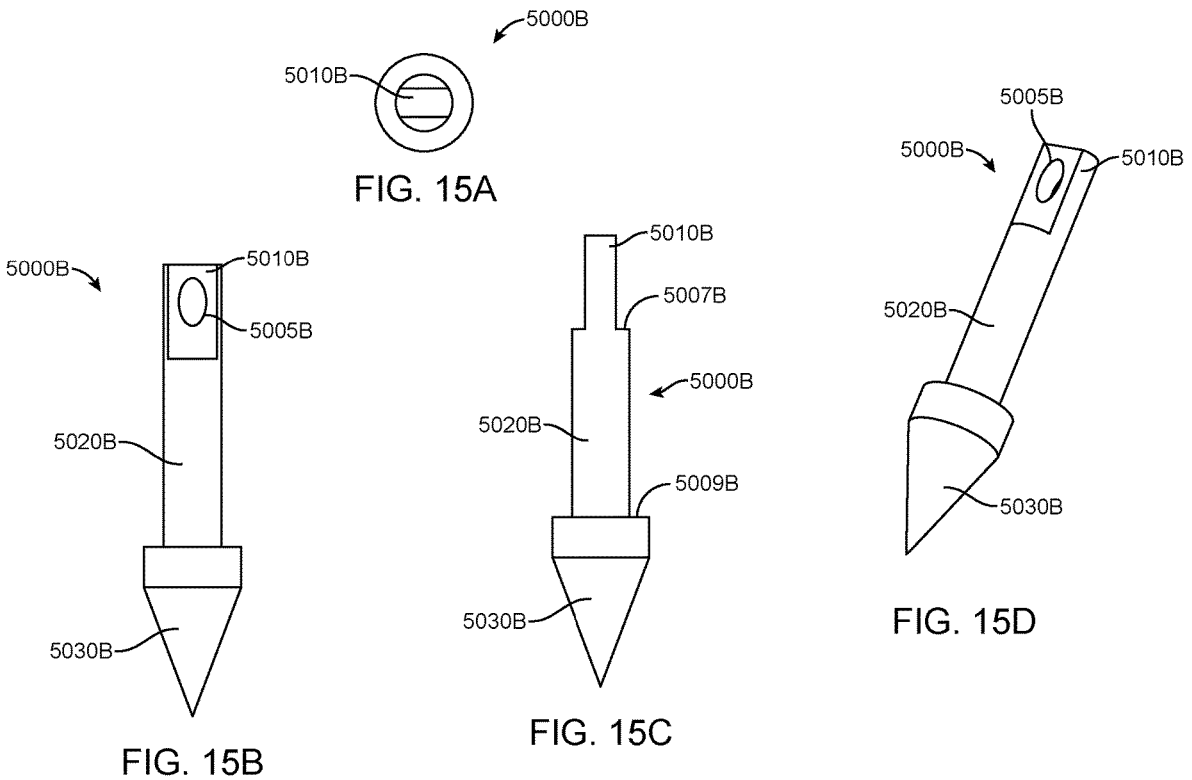

FIG. 14E provides a perspective view of a needle holder 2003B and FIG. 14F provides an end view of needle holder 2003B. FIG. 14G provides a perspective view of a needle catcher 2004B. FIG. 14H provides a perspective view of left catcher 2005B, FIG. 14I provides a perspective view of right catcher 2006B, and FIG. 14I provides a perspective view of center notch 2007B. In operation, the user can place a needle in the top handle and/or needle catcher 2004B. As shown in FIG. 15B, the needle 5000B can have a hole or aperture 5005B which is configured to receive a suture therethrough. When the device is closed, a ramped surface on the needle (e.g. on the needle tip portion 5030B) and a ramped surface 2017B on the center notch 2007B act in cooperation (e.g. as the needle slides past the center notch) to actuate a needle grasping function, such that once the ramped surface of the needle passes the ramped surface of the notch, the needle cannot be retracted out of the space or aperture 2002B of needle holder 2003B (e.g. as a proximal flat section 5007B or distal flat section 5009B of the needle becomes engaged with a flat section 2027B of the center notch), and subsequently when the device is opened the needle remains engaged needle holder 2003B and becomes unengaged from the needle catcher 2004B, and hence the suture which is retained within the eyelet or aperture 5005B of the needle is effectively transferred to the first jaw 2038B (which may be the lower jaw). In this way, the needle can be transferred from the top handle (or jaw) to the bottom handle (or jaw) and then the opening of the device allows the proximal portion of the needle and the suture to pass through the tissue.

FIGS. 15A to 15D depict different views of a needle 5000B of an automatic suture device. As shown here, needle 5000B includes an attachment portion 5010B, a body portion 5020B, and a tip portion 5030B.

In some embodiments, a needle can include an aperture or channel for receiving one or more sutures. For example, FIG. 16A depicts a needle 5000C having an aperture 5010C that receives or engages one or more sutures 5020C, 5030C. In some cases, needle 5000C can be used with a device that has a channel that is configured to receive multiple sutures. Likewise, FIG. 16B depicts a needle 5000D having a channel or aperture 5010D that receives or engages one or more sutures 5020D, 5030D. Such a needle assembly, which can include a needle and one or more sutures, can include any number of sutures.

In some embodiments, a device can include a canted coil that engages the needle. In some cases, the canted coil can engage or capture the needle in a jaw or other component of the device. In some cases, a canted coil can capture the needle in a bottom handle of the device. As shown in FIG. 17A, automatic suture device 2000E includes a distal end 2010E having a top jaw 2020E and a bottom jaw 2030E. The bottom jaw 2030E includes an aperture or chamber 2035E. A needle 5000E of the device is engaged with or held by top jaw 2020E, and a suture 2040E is coupled with the needle 5000E. A canted coil 2050E of the device is engaged with or held by bottom jaw 2030E. Similarly, as shown in FIG. 17B, automatic suture device 2000F includes a distal end 2010F having a top jaw 2020F and a bottom jaw 2030F. The bottom jaw 2030F includes an aperture or chamber 2035F. A needle 5000F of the device is engaged with or held by top jaw 2020F, and one or more sutures can be coupled with the needle 5000F, for example one or more sutures can be threaded through an aperture 5010F of the needle. A canted coil 2050F of the device is engaged with or held by bottom jaw 2030F. For example, coil 2050F can be situated in an annular recess or groove 2037F of the bottom jaw 2030F. In operation, as the top handle or top jaw closes or approaches or engages with the bottom handle or bottom jaw, the needle passes through the canted coil spring. As depicted in FIG. 17A, the needle 5000E can include a needle groove 5020E that engages the coil 2050E, and this engagement allows the canted coil spring 2050E to capture the needle 5000E, for example by constricting or compressing the needle. The needle can be released from the top handle or jaw, and in this way the needle can be captured in the bottom handle or bottom jaw by the canted coil spring.

FIG. 18A depicts an embodiment of a suture device 2000G that includes a top handle or jaw 2020G and a bottom handle or jaw 2030G. As shown in FIG. 18B, the device includes a needle 5000G engaged with the bottom handle or jaw 2030G. The needle 5000G is engaged with or coupled to a suture 5010G. The bottom handle or jaw 2030G can include a channel or passageway 2035A in which the suture can be positioned. The bottom handle or jaw 2030G can be slidably connected to or coupled with the top handle or jaw 2020G, such that the bottom handle or jaw 2030G can move distally and/or proximally relative to the top handle or jaw 2020G as indicated by arrow A. The top handle or jaw 2020G can include a channel or aperture 2025G that is configured to at least partially receive the needle 5000G when the needle 5000G is disposed in a distal location. In some cases, needle 5000G protrudes from the bottom handle or jaw 2030G. In some cases, aperture or channel 2025G is configured to receive and capture needle 5000G. In some cases, a main body 2021G of the top handle or jaw 2020G includes a longitudinal axis 2022G, and the channel or aperture 2025G includes a longitudinal axis 2026G, and longitudinal axis 2022G and longitudinal axis 2026G are parallel with one another. In some cases, a main body 2021G of the top handle or jaw 2020G includes a longitudinal axis 2022G, and the channel or aperture 2035G includes a longitudinal axis 2036G, and longitudinal axis 2022G and longitudinal axis 2036G are parallel with one another. In some embodiments, the top handle 2020G has a channel 2025G with a longitudinal axis 2026G, and the needle 5000G is situated in the channel 2035G of the bottom handle 2030G, the channel of the bottom handle having a longitudinal axis 2035G that is axially aligned with the longitudinal axis of the channel of the top handle.

FIG. 19A depicts an embodiment of a suture device 2000H that includes a first jaw 2020H (e.g. on a top handle) and a second jaw 2030H (e.g. on a bottom handle). As shown in the cross-section end view of FIG. 19B, the device can include multiple needles (e.g. first needle 5000H and second needle 5005H) that are engaged to or coupled with the first jaw 2020H. The second jaw 2030H can include one or more receiving elements (e.g. first channel 5010H and second channel 5015H) for receiving needles. For example, as shown here, first channel 5010H is configured to receive first needle 5000H and second channel 5015H is configured to receive second needle 50005H.

FIG. 20A depicts a needle assembly 5020I having a needle 5000I and a suture 5010I. a distal portion 5012I of the suture is coupled with a proximal portion 5002I of the needle. For example, the distal portion of the suture can be affixed to the needle by crimping or adhesive. FIG. 20B depicts another embodiment of a needle assembly 5020J having a needle 5000J and a suture 5010J. As can be seen, embodiments of the present invention can encompass needle assemblies where one end of the suture is fixed to the proximal end of the needle.

Figures 21A, 21B:
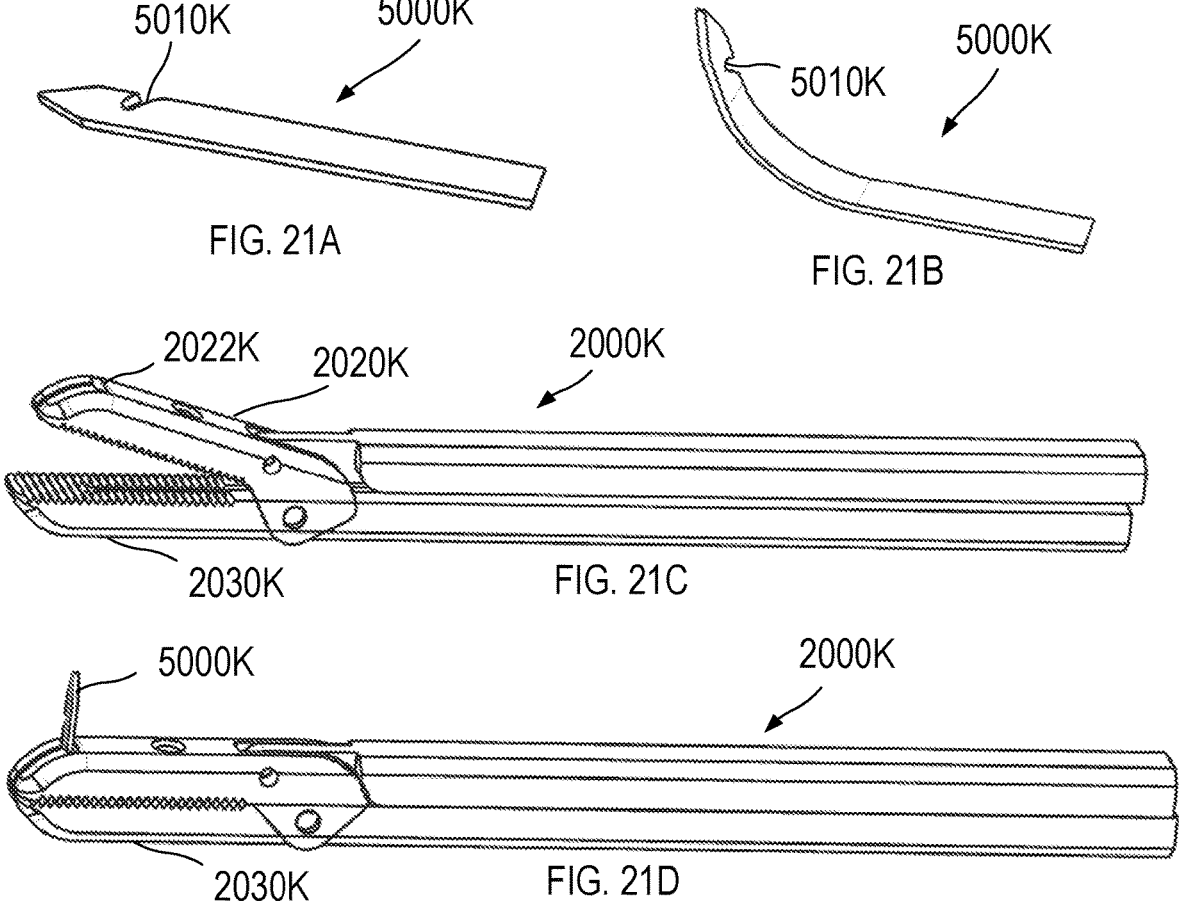

FIGS. 21A and 21B depict a flexible needle 5000K. In this embodiment, the needle 5000K includes an inclined surface or notch 5010K that is configured to engage or capture a suture. FIGS. 21C and 21D illustrate aspects of a suture device 2000K that can be used with a flexible needle 5000K. The flexible needle 5000K can be passed through a bottom handle 2030K of the device. When the needle 5000K is advanced distally, it protrudes substantially perpendicular to the long axis of the bottom handle and up through an aperture 2022K of the top handle 2020K. The top handle can be configured to hold a suture, and the needle can be configured to capture the suture. As the needle 5000K is retracted the suture can pass through the tissue. In some embodiments, the needle 5000K is made from or includes a superelastic material such as nitinol. In some cases, the needle 5000K has an inclined surface to capture the needle.

FIG. 22 illustrates aspects of a suture device 2000L that can be used with a flexible needle 5000L. The flexible needle 5000L can be passed through a bottom handle 2030L of the device. When the needle 5000L is advanced distally, for example through a channel 2035L of the bottom handle 2030L, it protrudes substantially perpendicular to the long axis of the bottom handle, through tissue, and up through an aperture 2022L of the top handle 2020L. For example, the channel 2035L can include a curve or a ramp 2037L which causes the distally advancing needle to bend toward the top handle. The top handle can be configured to hold a suture 2160L, and the needle can be configured to capture the suture. As the needle 5000L is retracted proximally the suture can pass through the tissue. In some embodiments, the needle 5000L is made from or includes a superelastic material such as nitinol. In some cases, the needle 5000L has an opening 5015L with an inclined surface, edge, or notch 5010L that is configured to engage or capture the suture 2160L. The inclined edge 5010L can guide the suture through the opening 5015L. As shown here, suture 2160L can be threaded through a lateral passageway 2025L of the top handle 2020L, which allows the suture to pass through the aperture 2022L where it can be engaged by the needle 5000L.

In some embodiments, top handle 2020L is configured to clamp the tissue (e.g. in cooperation with bottom handle 2030L) and hold the suture 2160L. Device 2000L can include an elongate member 2040L disposed in the bottom handle, and a deployment trigger 2050L in operative association with the elongate member 2040L, such that when the user advances or activates the deployment trigger, the deployment trigger 2050L in turn deploys the elongate member 2040L thereby enabling the needle 5000L to capture the suture 2160L from the top handle 2020L. In some cases, the elongate member 2040L is coupled with the needle 5000L. In some cases, the elongate member 2040L and the needle 5000L are a single monolithic element, and can be referred to in the alternate as either an elongate member or a needle. Hence in some embodiments an elongate member can include a superelastic metal, such as nitinol. Likewise, an elongate member can include an inclined surface or notch that is configured to engage or capture a suture.

In some embodiments, the elongate member 2040L is curved when in a resting state, and can be straightened in an elastically deformed state, when any portion of the elongate member 2040L is positioned within the straight section 2034L of the channel 2035L, that portion of the elongate member 2034L is elastically deformed to a straightened configuration. In other words, the elongate member can have a curved shape in the default state, and can have a straight shape when in an undeployed configuration. Likewise, a needle can be curved in the default or resting state, and when the needle is in the handle (e.g. in the channel 2035L) it can elastically deform to a straight position.

Figure 23A:
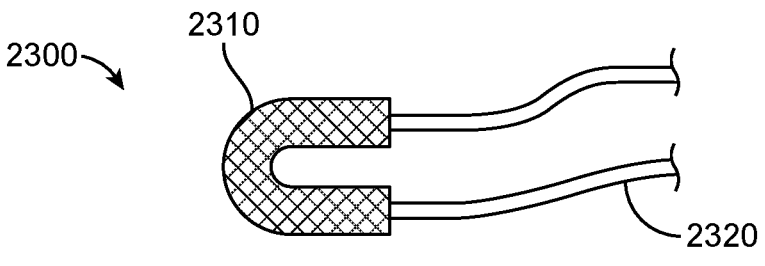
Figure 23B:
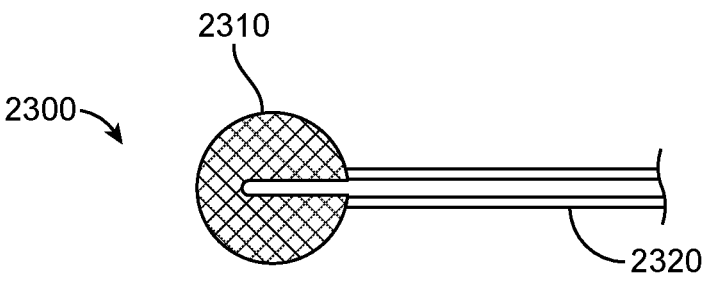
Figure 23C:
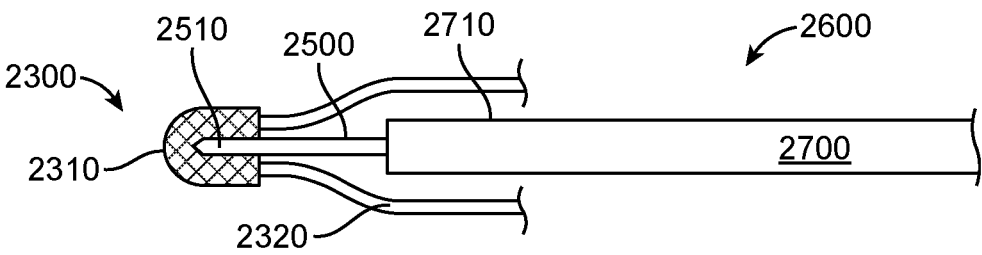
Figure 23D:
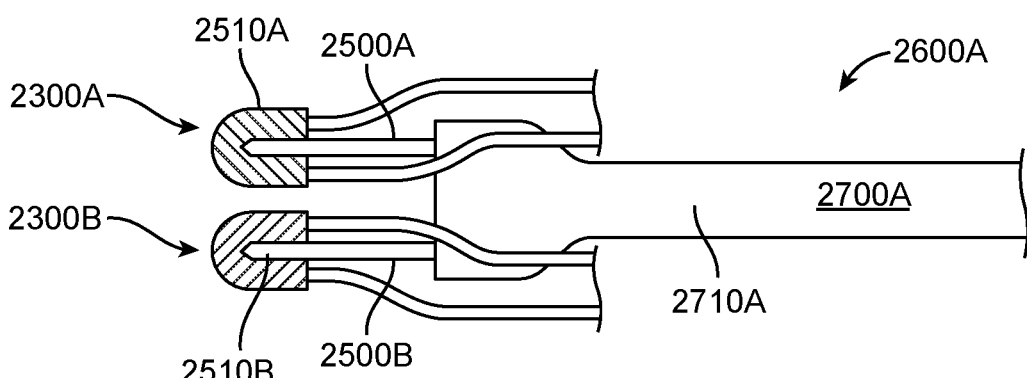

FIGS. 23A and 23B depict aspects of a suture assembly 2300 according to embodiments of the present invention. A suture assembly 2300 can include a braided sleeve 2310 and a suture 2320 which passes through the braided sleeve. FIG. 23A depicts the braided sleeve 2310 or suture anchor in an uncompressed state, and FIG. 23B depicts the braided sleeve 2310 or suture anchor in a compressed state. As illustrated in FIG. 23C, a suture anchor 2300 can be coupled with or attached to a distal end 2510 of a needle 2500 of a device 2600. The needle protrudes from the distal end 2710 of the handle 2700 of the device 2600. As illustrated in FIG. 23D, a first suture anchor 2300A can be coupled with or attached to a distal end 2510A of a first needle or elongate member 2500A of a device 2600A. The first needle or elongate member 2500A protrudes from the distal end 2710A of the handle 2700A of the device 2600A. A second suture anchor 2300B can be coupled with or attached to a distal end 2510B of a second needle or elongate member 2500B of the device 2600A. The second needle or elongate member 2500B protrudes from the distal end 2710A of the handle 2700A of the device 2600A.

Figure 23E:
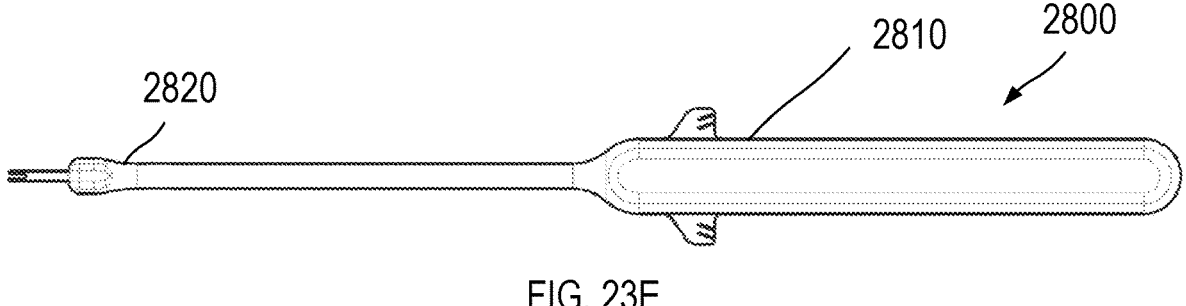
Figure 23F:
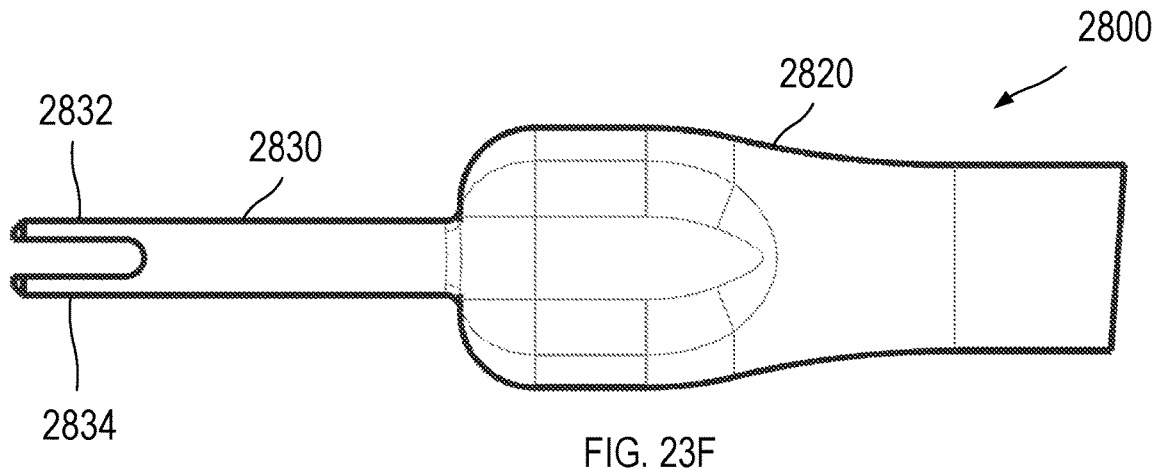
Figure 23G:
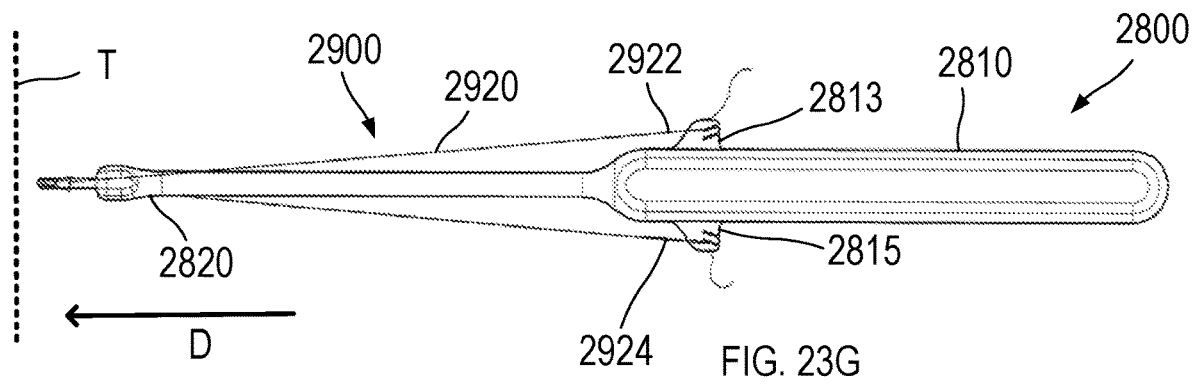
Figure 23H:
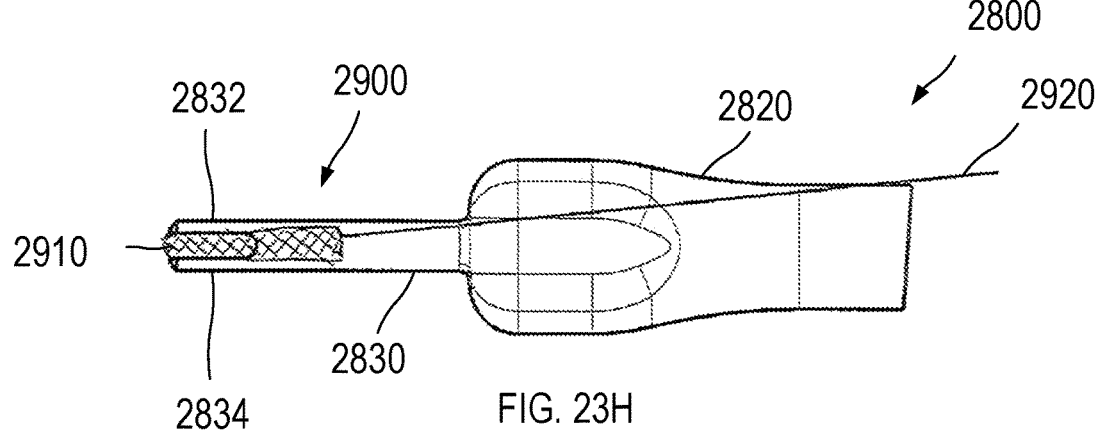
Figure 23I:
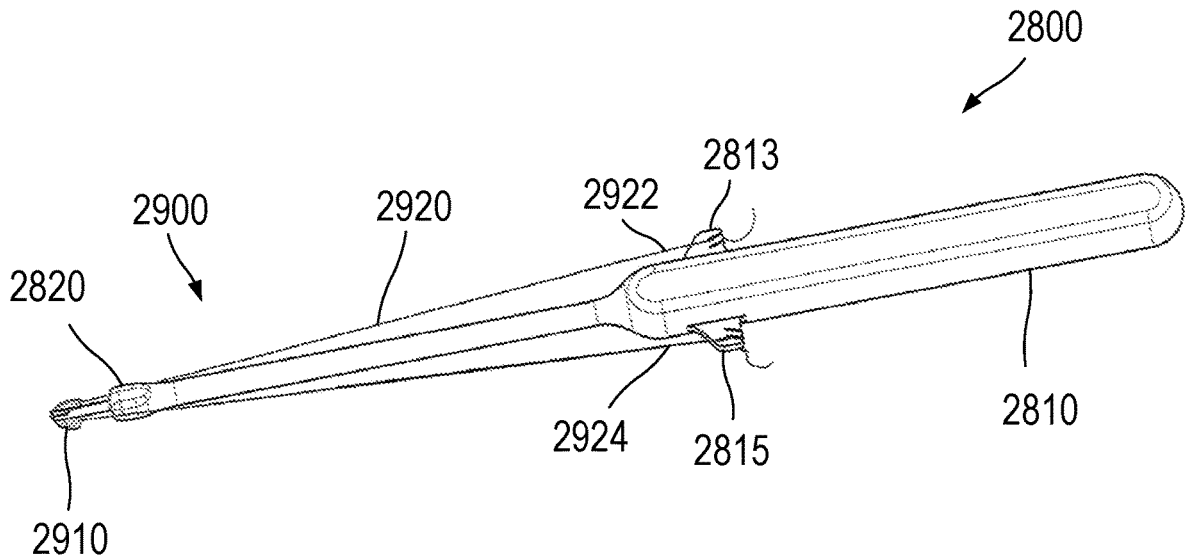
Figures 24A, 24B:
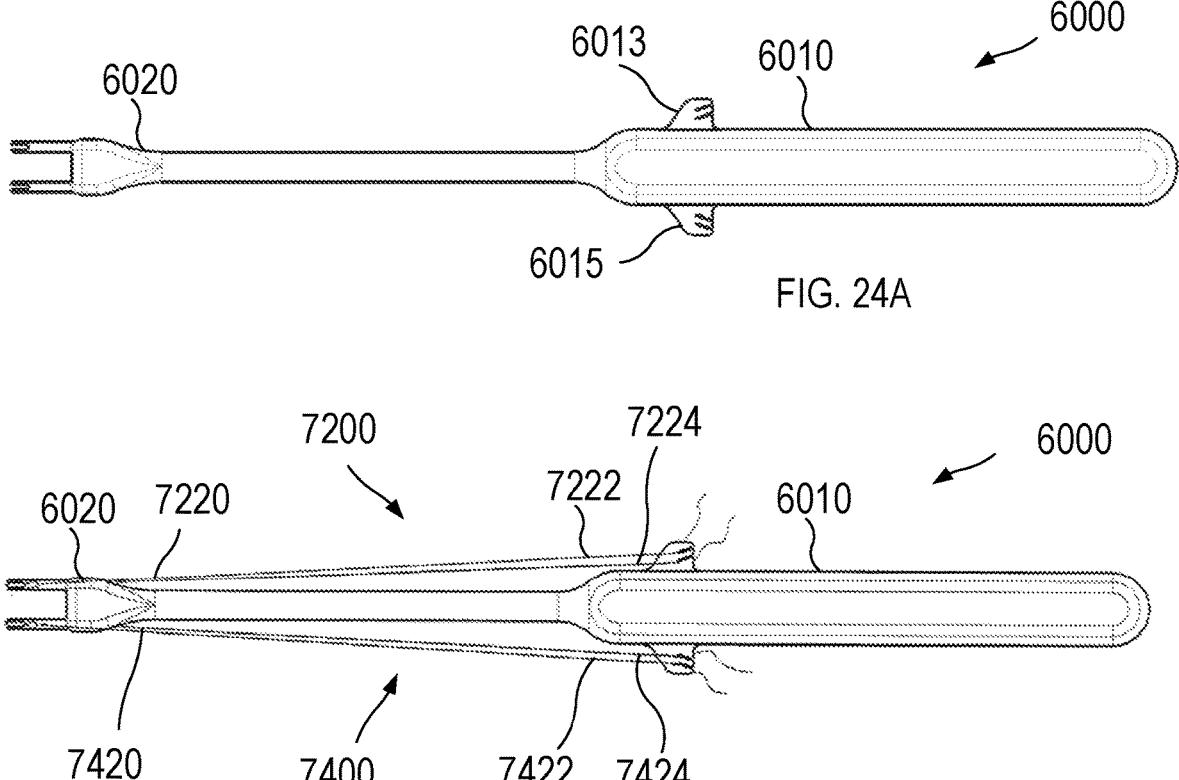
Figure 24C:
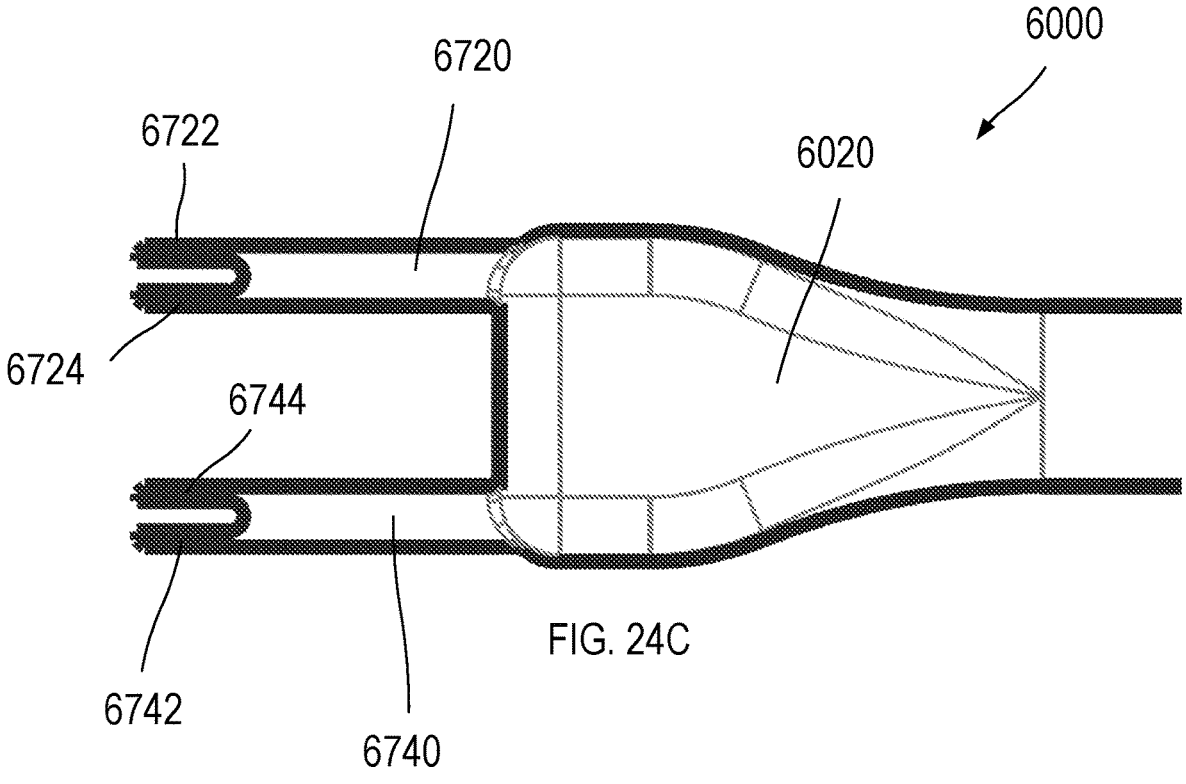
Figures 24D, 24E:
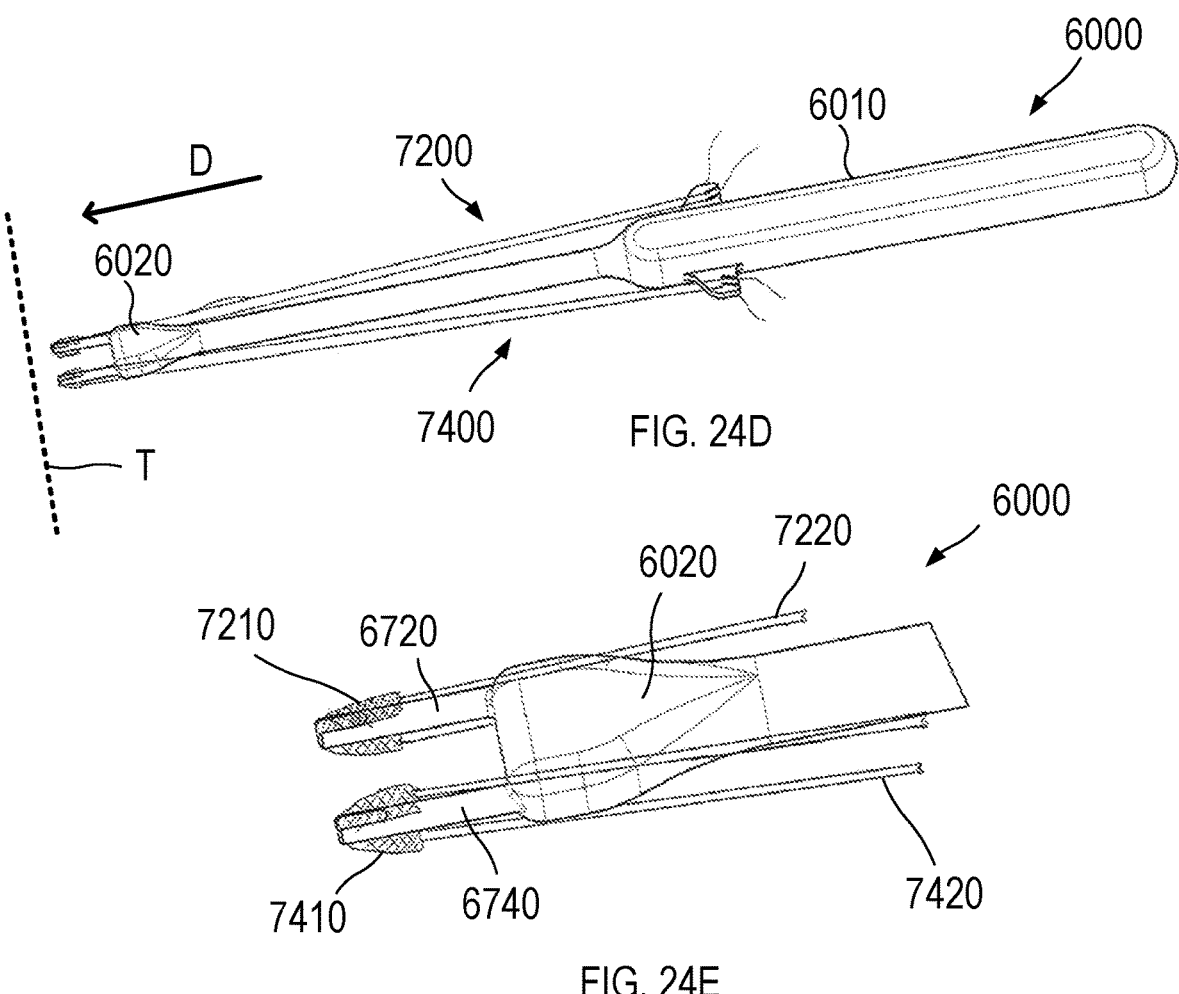
Figure 24F:
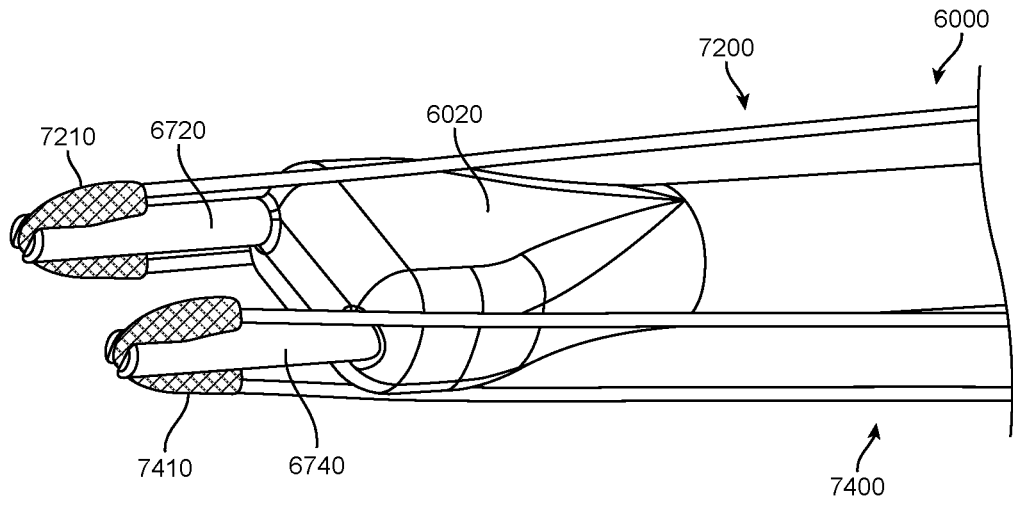

FIGS. 23E and 23F depict aspects of a single anchor suture device 2800. As shown here, the suture device 2800 has a handle 2810 with a distal end 2820. In operation, a suture anchor can be coupled with an anchor support 2830 of the distal end 2820. For example, a braided sleeve of a suture anchor can be placed between or against a first prong 2832 of the support and a second prong 2834 of the support. FIGS. 23G to 23I depict further aspects of the single anchor suture device 2800. As shown here, the suture device can be coupled to or loaded with an anchor suture 2900 that includes a braided sleeve 2910 and a suture 2920. A first end 2922 of the suture 2920 can be coupled with or wrapped about a first wing 2813 of the handle 2810, and a second end 2924 of the suture 2910 can be coupled with or wrapped about a second wing 2815 of the handle 2810. The braided sleeve 2910 of the suture anchor 2900 is placed between or against the first prong 2832 of the support 2830 and the second prong 2834 of the support 2830. In some embodiments, the suture anchor 2900 includes a braided sleeve 2910 that is configured to receive the suture 2920, and the braided sleeve 2910 can be configured to bunch up when tension is applied to the suture 2920. In operation, the user can advance the device in a distal direction so as to push the distal prongs of the support 2830 through a tissue or to a distal side of a tissue. In this way, the braided sleeve 2910 can also be passed through the tissue or to a distal side of the tissue. When the suture 2920 is retracted proximally the braided sleeve 2910 does not proximally pass through the tissue again, but rather remains in place on the other side. The operator can pull or apply tension to the suture running through the braided sleeve, thereby shortening the length of the braided sleeve causing it to bunch up. In other words, the ends of the braided sleeve do not pass back through the tissue and the shortening of length causes the braided sleeve to expand laterally (the bunching). The two ends of the suture can then be tied or fixed in some other manner to attach the soft tissue.

FIGS. 24A to 24F depict aspects of a double anchor suture device 6000. As shown here, the suture device 6000 has a handle 6010 with a distal end 6020. In operation, a first anchor suture 7200 can be coupled with a first anchor support 6720 of the distal end 6020 and a second anchor suture 7400 can be coupled with a second anchor support 6740 of the distal end 6020. For example, a braided sleeve 7210 of the first suture anchor 7200 can be placed between or against a first or lateral prong 6722 of the support 6720 and a second or medial prong 6724 of the support 6720. Similarly, a braided sleeve 7410 of the second suture anchor 7400 can be placed between or against a first or lateral prong 6742 of the support 6740 and a second or medial prong 6744 of the support 6740. A first end 7222 of the first suture 7220 can be coupled with or wrapped about a first wing 6013 of the handle 6010, and a second end 7224 of the first suture 7220 can also be coupled with or wrapped about the first wing 2813 of the handle 6010. Likewise, a first end 7422 of the second suture 7420 can be coupled with or wrapped about a second wing 6015 of the handle 2810, and a second end 7424 of the second suture 7420 can also be coupled with or wrapped about the second wing 2815 of the handle 6010.

In embodiments shown in FIGS. 23A-23I, a device can be operated by a user to place a suture in the patient tissue by for example manipulating the device with the handle. The distal tip of the device (e.g. needle or prongs) can be configured to receive the braided sleeve. The ends of the suture can be fixed to the handle with a suture attachment or wing. In some embodiments, the suture can be fixed by cleats. The anchor can be deployed by pushing the tip of the needle or prongs in a distal direction as indicated by arrow D through the tissue T until the braided sleeve is on the farside or distal side of the tissue. To deploy the anchor, the suture ends are removed from the suture attachment on the handle and tension is applied to the suture to expand the braided as described elsewhere herein.

In embodiments shown in FIGS. 24A-24F, a device can be operated by a user to simultaneously place multiple sutures in the patient tissue by for example manipulating the device with the handle. As shown here, two needles or two prong pairs can be disposed at the distal tip of the device. Each needle or prong pair can be configured to receive a suture anchor. The suture ends of each anchor can be fixed to a suture attachment, such as a suture cleat or wing. The anchors can be deployed by pushing the tip of the needles or prong pairs in a distal direction as indicated by arrow D through the tissue T until the braided sleeves are on the farside or distal side of the tissue. To deploy the anchors, the suture ends are removed from the suture attachment on the handle and tension is applied to the sutures to expand the braided as described elsewhere herein.

FIGS. 25A and 25B depicts aspects of a suture device 3400, according to embodiments of the present invention. As shown here, device 3400 includes a distal portion 3410.

All features of the described systems and devices are applicable to the described methods mutatis mutandis, and vice versa. Embodiments of the present invention encompass kits having suture devices or systems as disclosed herein. In some embodiments, the kit includes one or more systems for suture retrieval, along with instructions for using the system for example according to any of the methods disclosed herein.

Each reference provided herein in incorporated by reference in its entirety to the same extent as if each reference were individually incorporated by reference. Relatedly, all publications, patents, patent applications, journal articles, books, technical references, and the like mentioned in this specification are herein incorporated by reference to the same extent as if each individual publication, patent, patent application, journal article, book, technical reference, or the like was specifically and individually indicated to be incorporated by reference.

Although embodiments of the present invention have been explained in relation to one or more preferred embodiments, it is to be understood that many other possible modifications and variations can be made without departing from the spirit and scope of the invention.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

In this detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although the foregoing invention has been described in some detail by way of illustration and example for purposes of clarity of understanding, one of skill in the art will appreciate that certain changes, modifications, alternate constructions, and/or equivalents may be practiced or employed as desired, and within the scope of the appended claims. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components. It is intended that the following claims define the scope of the invention and that methods and structures within the scope of these claims and their equivalents be covered thereby.

What is claimed is:

1. An automatic suture device comprising:

a needle having a proximal portion and a distal portion, the distal portion of the needle comprising distal a flat section and a needle tip portion with a ramped surface, the proximal portion of the needle comprising a proximal flat section and an opening configured to receive a suture;

a distal end comprising a flat section, a ramped surface, and an aperture capable of receiving the needle;

a proximal end comprising a top handle and a bottom handle; and a connector comprising a hinge that is at a position between the distal end and the proximal end, wherein the hinge allows for pivoting movement of the top handle and the bottom handle, wherein the ramped surface of the needle is configured to slidingly engage the ramped surface of the distal end to actuate a needle grasping function, wherein the flat section of the distal end is configured to engage the distal flat section of the needle to prevent retraction of the needle from the aperture after the distal flat section is advanced past the ramped surface, and wherein the flat section of the distal end is configured to engage the proximal flat section of the needle to prevent retraction of the needle from the aperture after the proximal flat section is advanced past the ramped surface.

2. The automatic suture device of claim 1, wherein the needle tip portion comprises a distal conical section, and wherein the ramped surface is disposed on the distal conical section.

3. The automatic suture device of claim 1, wherein the needle tip portion comprises a proximal cylindrical section and a distal conical section, wherein the flat section of the needle is disposed on a proximal surface of the proximal cylindrical section, and wherein the ramped surface is disposed on the distal conical section.

* * * * *